US011434195B2

(12) United States Patent
Svetlov

(10) Patent No.: US 11,434,195 B2
(45) Date of Patent: Sep. 6, 2022

(54) COMPOSITIONS AND METHODS FOR TREATMENT OF CENTRAL NERVOUS SYSTEM TUMORS

(71) Applicant: UNIVERSITY OF FLORIDA RESEARCH FOUNDATION, INC., Gainesville, FL (US)

(72) Inventor: Stanislav Igorevich Svetlov, Gainesville, FL (US)

(73) Assignee: UNIVERSITY OF FLORIDA RESEARCH FOUNDATION, INC., Orlando, FL (US)

( * ) Notice: Subject to any disclaimer, the term of this patent is extended or adjusted under 35 U.S.C. 154(b) by 96 days.

(21) Appl. No.: 16/632,721

(22) PCT Filed: Jul. 20, 2018

(86) PCT No.: PCT/US2018/043120
§ 371 (c)(1),
(2) Date: Jan. 21, 2020

(87) PCT Pub. No.: WO2019/018785
PCT Pub. Date: Jan. 24, 2019

(65) Prior Publication Data
US 2021/0130283 A1    May 6, 2021

Related U.S. Application Data

(60) Provisional application No. 62/668,549, filed on May 8, 2018, provisional application No. 62/534,992, filed on Jul. 20, 2017.

(51) Int. Cl.
*C07C 217/28* (2006.01)
*A61K 31/133* (2006.01)

(52) U.S. Cl.
CPC .......... *C07C 217/28* (2013.01); *A61K 31/133* (2013.01)

(58) Field of Classification Search
None
See application file for complete search history.

(56) References Cited

U.S. PATENT DOCUMENTS

| 8,686,008 B2 | 4/2014 | McCurdy et al. |
| 2011/0177108 A1 | 7/2011 | Svetlov et al. |

FOREIGN PATENT DOCUMENTS

| EP | 0037780 A1 | 10/1981 |
| WO | 2010017550 A2 | 2/2010 |
| WO | 2017031392 A1 | 2/2017 |
| WO | 2019018785 A2 | 1/2019 |

OTHER PUBLICATIONS

Cao et al., Cellular Oncology (2013), 36(3), pp. 247-257.*
PCT/US2018/043120, PCT Search Report & Written Opinion, dated Mar. 14, 2019, 12 pages.
Adkins, Jessica E. et al., "Mitragyna speciosa, A Psychoactive Tree from Southeast Asia with Opioid Activity", Current Topics in Medicinal Chemistry, 2011, vol. 11, pp. 1165-1175.
Babu, Kavita M. et al., "Opioid receptors and legal highs: Salvia divinorum and Kratom", Clinical Toxicology, 2008, vol. 46, No. 2, pp. 146-152.
Baumann, Brian C. et al., "Stereotactic Intracranial Implantation and In vivo Bioluminescent Imaging of Tumor Xenografts in a Mouse Model System of Glioblastoma Multiforme", Journal of Visualized Experiments, Sep. 2012, vol. 6, e4089, 14 pages.
Binda, Elena et al., "The EphA2 Receptor Drives Self-Renewal and Tumorigenicity in Stem-like Tumor-Propagating Cells from Human Glioblastomas", Cancer Cell, Dec. 11, 2012, vol. 22, pp. 765-780.
Bjornson, Christopher R. R. et al., "Turning Brain into Blood: A Hematopoietic Fate Adopted by Adult Neural Stem Cells in Vivo", Science, Jan. 22, 1999, vol. 283, No. 5401, pp. 534-537.
Boyer, Edward W. et al., "Self-treatment of opioid withdrawal using kratom (*Mitragynia speciosa korth*)", Addiction, Jun. 2008, vol. 103, No. 6, pp. 1048-1050.
Brewer, Gregory J. et al., "Human primary brain tumor cell growth inhibition in serum-free medium optimized for neuron survival", Brain Research, 2007, vol. 1157, pp. 156-166.
Calvani, Maura et al., "Norepinephrine promotes tumor microenvironment reactivity through β3-adrenoreceptors during melanoma progression", Oncotarget, Dec. 6, 2014, vol. 6, No. 7, pp. 4615-4632.
Cao, Mengde et al., "Composite fatty acid ether amides suppress growth of liver cancer cells in vitro and in an in vivo allograft mouse model", Cell Oncol (Dordr), Jun. 2013, vol. 36, No. 3, pp. 247-257.
Chen, Xueran et al., "EZH2 Palmitoylation Mediated by ZDHHC5 in p53-Mutant Glioma Drives Malignant Development and Progression", Cancer Research, Sep. 15, 2017, vol. 77, No. 18, pp. 4998-5011.
Chiang, Po-Chang et al., "A Formulation-Enabled Preclinical Efficacy Assessment of a Farnesoid X Receptor Agonist, GW4064, in Hamsters and Cynomolgus Monkeys", Journal of Pharmaceutical Sciences, Nov. 2011, vol. 100, No. 11, pp. 4722-4733.

(Continued)

*Primary Examiner* — Brian J Davis
(74) *Attorney, Agent, or Firm* — Timothy H. Van Dyke; Wolter, Van Dyke, Davis, Pllc.

(57) ABSTRACT

Compounds, pharmaceutical compositions, and methods for treating cancer, in particular brain cancer, are provided, including amphiphilic fatty acid/alcohol ethers (AIPs) comprising endocannabinoid and FABP motifs covalently linked to a beta-adrenoreceptor antagonist motif in one molecule. The invention includes methods for inhibiting growth of brain cancer cells by contacting the compound(s) with brain cancer cells. The invention provides a method for treating both brain cancer and brain cancer metastases, and for suppression of regrowth of brain cancer cells after radiation, surgical treatment, or chemotherapy of brain cancer. The invention also comprises an optimized chemical synthesis of the AIP compounds and methods of using the compounds, alone or in combination with another agent, for suppressing the growth of brain cancer cells, and enhancing survival of normal CNS cells, or improving recuperation from radiation, surgical or chemotherapy.

12 Claims, 15 Drawing Sheets

Specification includes a Sequence Listing.

(56) References Cited

OTHER PUBLICATIONS

Davis, Brad et al., "Comparative genomic and genetic analysis of glioblastoma-derived brain tumor-initiating cells and their parent tumors", Neuro-Oncology, 2016, vol. 18, No. 3, pp. 350-360.
Davis, Mary Elizabeth, "Glioblastoma: Overview of Disease and Treatment", Clin J Oncol Nurs, Oct. 1, 2016, vol. 20, No. 5, S2-S8, 14 pages.
Day, Bryan W. et al., "EphA3 Maintains Tumorigenicity and Is a Therapeutic Target in Glioblastoma Multiforme", Cancer cell, Feb. 11, 2013, vol. 23, pp. 238-248.
Deleyrolle, Loic P. et al., "Evidence for label-retaining tumour-initiating cells in human glioblastoma", Brain, 2011, vol. 134, pp. 1331-1343.
Deleyrolle, Loic P. et al., "Determination of Somatic and Cancer Stem Cell Self-Renewing Symmetric Division Rate Using Sphere Assays", PLoS One, 2011, vol. 6, issue 1, e15844, pp. 1-11.
Festuccia, Claudio et al.,"The first-in-class alkylating deacetylase inhibitor molecule tinostamustine shows antitumor effects and is synergistic with radiotherapy in preclinical models of glioblastoma", Journal of Hematology & Oncology, 2018, vol. 11, No. 32, 19 pages.
Fotovati, Abbas et al.,"YB-1 Bridges Neural Stem Cells and Brain Tumor-Initiating Cells via Its Roles in Differentiation and Cell Growth" Cancer Res, 2011, vol. 71, pp. 5569-5578.
Franceschi, Enrico et al., "Pharmacotherapy of Glioblastoma: Established Treatments and Emerging Concepts", CNS Drugs, 2017, vol. 31, pp. 675-684.
Friedmann-Morvinski, Dinorah et al., "Overexpression Models: Lentiviral Modeling of Brain Cancer", Mouse Biology, Jun. 2013, vol. 3, pp. 121-139.
Gravina, Giovanni Luca et al., "The novel CXCR4 antagonist, PRX177561, reduces tumor cell proliferation and accelerates cancer stem cell differentiation in glioblastoma preclinical models", Tumor Biology, Jun. 2017, pp. 1-17.
Gua, Pin et al., "C-Myc negatively controls the tumor suppressor PTEN by upregulating miR-26a in glioblastoma multiforme cells", Biochemical and Biophysical Research Communications, 2013, vol. 441, pp. 186-190.
Haris, Sarika Prabhu et al., "o-Naphthalenedicarboxaldehyde Derivative of 7¢-Aminonaltrindole as a Selective ä-Opioid Receptor Affinity Label", J. Med Chem., 2007, vol. 50, pp. 3392-3396.
He, Jing Jing et al., "Activation of β-adrenergic receptor promotes cellular proliferation in human glioblastoma", Oncology Letters, 2017, vol. 14, pp. 3846-3852.
Hitomi, Masahiro et al., "Differential Connexin Function Enhances Self-Renewal in Glioblastoma", Cell Rep., May 19, 2015, vol. 11, No. 7, pp. 1031-1042.
James, Michelle et al., "A New Positron Emission Tomography (PET) Radioligand for Imaging Sigma-1 Receptors in Living Subjects", J Med Chem., Oct. 11, 2012, vol. 55, No. 19, pp. 8272-8282.
James, Michelle L. et al., "Evaluation of σ-1 Receptor Radioligand 18F-FTC-146 in Rats and Squirrel Monkeys Using PET", J Nucl Med., Jan. 2014, vol. 55, No. 1, pp. 147-153.
Jarzabek, Monika A. et al., "In Vivo Bioluminescence Imaging Validation of a Human Biopsy-Derived Orthotopic Mouse Model of Glioblastoma Multiforme", Molecular Imaging, May 2013, vol. 12, No. 3, pp. 161-172.
Journigan, V. Blair et al., "Nonpeptide Small Molecule Agonist and Antagonist Original Leads for Neuropeptide FF1 and FF2 Receptors", J. Med. Chem., 2014, vol. 57, pp. 8903-8927.
Kane, Brian E et al., "Toward a Structure-Based Model of Salvinorin A Recognition of the K-Opioid Receptor", J. Med. Chem., 2008, vol. 51, pp. 1824-1830.
Kane, Brian E et al., "A unique binding epitope for salvinorin A, a non-nitrogenous kappa opioid receptor agonist", FEBS Journal, 2006, vol. 273, pp. 1966-1974.
Kato, Hideaki et al., "Functional Evaluation of p53 and PTEN Gene Mutations in Gliomas", Clinical Cancer Research, Oct. 2000, vol. 6, pp. 3937-3943.

Kim, Woong et al., "Real-time imaging of glioblastoma using bioluminescence in a U-87 MG xenograft model mouse", J Korean Soc Appl Biol Chem, 2015, vol. 58, No. 2, pp. 243-248.
Küçüktürkmen, Brian et al., Drug Development and Industrial Pharmacy, 2018, vol. 44, No. 2, pp. 306-315.
Linkous, Amanda G. et al., "Cytosolic Phospholipase A2 and Lysophospholipids in Tumor Angiogenesis", Articles, Sep. 22, 2010, vol. 108, issue 18, pp. 1398-1412.
Louis, Sharon A. et al., "Enumeration of Neural Stem and Progenitor Cells in the Neural Colony-Forming Cell Assay", Stem Cells, 2008, vol. 26, pp. 988-996.
Luchman, H. Artee et al., "Dual mTORC1/2 Blockade Inhibits Glioblastoma Brain Tumor Initiating Cells In Vitro and In Vivo and Synergizes with Temozolomide to Increase Orthotopic Xenograft Survival", Clin Cancer Res, Nov. 15, 2014, vol. 20, No. 22, pp. 5756-5767.
Mankus, Jessica V. et al., "Nonpeptide ligands of neuropeptide FF: current status and structural insights", Future Med Chem., Jun. 2012, vol. 4, No. 9, pp. 1085-1092.
Martuscello, Regina T. et al., "A Supplemented High-Fat Low-Carbohydrate Diet for the Treatment of Glioblastoma", Clin Cancer Res, May 15, 2016, vol. 22, No. 10, pp. 2482-2495.
McCurdy, Christopher R. et al., "Investigation of Phenolic Bioisosterism in Opiates: 3-Sulfonamido Analogues of Naltrexone and Oxymorphone", Organic Letters, 2000, vol. 2, No. 6, pp. 819-821.
McCurdy, Christopher R. et al., "Naphthalene Dicarboxaldehyde as an Electrophilic Fluorogenic Moiety for Affinity Labeling: Application to Opioid Receptor Affinity Labels with Greatly Improved Fluorogenic Properties", Journal of Medicinal Chemistry, Jul. 4, 2002, vol. 45, No. 14, pp. 2887-2890.
McCurdy, Christopher R. et al.,"Antinociceptive profile of salvinorin A, a structurally unique kappa opioid receptor agonist", Pharmacology, Biochemistry and Behavior, 2006, vol. 83, pp. 109-113.
McDowell, Kelli A. et al., "Targeting the AKT Pathway in Glioblastoma" Current Pharmaceutical Design, 2011, vol. 17, pp. 2411-2420.
Mésangeau, Christophe et al., "Conversion of a Highly Selective Sigma-1 Receptor-Ligand to Sigma-2 Receptor Preferring Ligands with Anticocaine Activity", J. Med. Chem., 2008, vol. 51, pp. 1482-1486.
Messali, Andrew et al., "A Review of the Economic Burden of Glioblastoma and the Cost Effectiveness of Pharmacologic Treatments", PharmacoEconomics, 2014, vol. 32, pp. 1201-1212.
Miller, Kimberly D. et al., "Cancer Treatment and Survivorship Statistics, 2016", CA Cancer J Clin, 2016vol. 66, pp. 271-289.
Montoya, Alexa et al., "Use of non-selective β-blockers is associated with decreased tumor proliferative indices in early stage breast cancer", Oncotarget, 2017, vol. 8, No. 4, pp. 6446-6460.
Okonogi, Noriyuki et al.,"Topics in Chemotherapy, Molecular-targeted Therapy, and Immunotherapy for Newly-diagnosed Glioblastoma Multiforme", Anticancer Research, Mar. 2015, vol. 35, pp. 1229-1236.
European Search Report for Application No. 11835124.1; dated Feb. 26, 2021, 6 pages.
Byun, Hoe-Sup et al., "A two-step synthesis of (R)- and (S)-Benzylglycidyl ether", Tetrahedron Letters, 1989, vol. 30, No. 21, pp. 2751-2754.
Cao, Mengde et al., "Composite tally acid ether amides suppress growth of liver cancer cells in vitro and in vivo allograft mouse model", Cell Oncol (Dordr), Jun. 2013, vol. 36, No. 3, pp. 247-257.
Ozawa, Tomoko et al., "Establishing Intracranial Brain Tumor Xenografts With Subsequent Analysis of Tumor Growth and Response to Therapy using Bioluminescence Imaging", J. Vis. Exp., Jul. 20101, vol. 41, e1986, 5 pages.
Pan, Wei Kang et al.,"Propranolol Induces Regression of Hemangioma Cells via the Down-Regulation of the PI3K/Akt/eNOS/VEGF Pathway", Pediatr Blood Cancer, 2015, vol. 62, pp. 1411-1420.
Paul-Samojedny, Monika et al.,"Knockdown of AKT3 (PKB?) and PI3KCA Suppresses Cell Viability and Proliferation and Induces the Apoptosis of Glioblastoma Multiforme T98G Cells", BioMed Research International, 2014, Article ID 768181, 12 pages.
Piccirillo, S.G.M. et al., "Bone morphogenetic proteins inhibit the tumorigenic potential of human brain tumour-initiating cells", Nature, Dec. 7, 2006, vol. 444, pp. 761-765.

(56) References Cited

OTHER PUBLICATIONS

Polivka JR., Jiri et al.,"Advances in Experimental Targeted Therapy and Immunotherapy for Patients with Glioblastoma Multiforme", Anticancer Research, 2017, vol. 37, pp. 21-0.34.
Qu, Jiagui et al., "Establishment and partial characterization of a human tumor cell line, GBM-HSF, from a glioblastoma multiforme", Human Cell, 2014, vol. 27, pp. 129-136.
Ray PhD, Saurabh et al., "Treatment Patterns, Survival, and Healthcare Costs of Patients with Malignant Gliomas in a Large US Commercially Insured Population", Am Health Drug Benefits, 2014, vol. 7, No. 3, pp. 140-149.
Reinartz, Roman et al.,"Functional Subclone Profiling for Prediction of Treatment-Induced Intra-Tumor Population Shifts and Discovery of Rational Drug Combinations in Human Glioblastoma", Clin Cancer Res., Jan. 15, 2017, vol. 23, No. 2, pp. 562-574.
Reynolds, Brent A. et al.,"Generation of Neurons and Astrocytes from Isolated Cells of the Adult Mammalian Central Nervous System", Science, Mar. 27, 1992, vol. 255, No. 5052, pp. 1707-1710.
Reynolds, Brent A. et al.,"A Multipotent EGF-Responsive Striatal Embryonic Progenitor Cell Produces Neurons and Astrocytes", The Journal of Neuroscience, Nov. 1992, vol. 12, No. 11, pp. 4565-4574.
Reynolds, Brent A. et al.,"Clonal and Population Analyses Demonstrate That an EGF-Responsive Mammalian Embryonic CNS Precursor Is a Stem Cell", Developmental Biology, 1996, vol. 175, No. 0090, pp. 1-13.
Reynolds, Brent A. et al.,"Neural stem cells and neurospheres—reevaluating the relationship", Nature Methods, May 2005, vol. 2 N 0.5, pp. 333-336.
Salphati, Laurent et al., "Brain Distribution and Efficacy of the Brain Penetrant PI3K Inhibitor GDC-0084 in Orthotopic Mouse Models of Human Glioblastoma", Drug Metab Dispos, Dec. 2016, vol. 44, pp. 881-1889.
Sautin, Yuri Y. et al., "Enhancement of survival by LPA via Erk1/Erk2 and PI 3-kinase/Akt pathways in a murine hepatocyte cell line",Am J Physiol Cell Physiol, 2001, vol. 281, pp. C2010-C2019.
Sautin, Yuri Y. et al., "Hepatic Oval (Stem) Cell Expression of Endothelial Differentiation Gene Receptors for Lysophosphatidic Acid in Mouse Chronic Liver Injury", Journal of Hematotherapy & Stem Cell Research, 2002, vol. 11, pp. 643-649.
Seminerio, Michael J. et al., "Synthesis and Pharmacological Characterization of a Novel Sigma Receptor Ligand with Improved Metabolic Stability and Antagonistic Effects Against Methamphetamine", The AAPS Journal, Mar. 2012, vol. 14, No. 1, pp. 46-51.
Sharif, Ariane et al., "Isolation and Culture of Human Astrocytes"Astrocytes: Methods and Protocols, Methods in Molecular Biology, 2012, vol. 814, pp. 137-151.
Shields, Lisa BE et al.,"Concurrent bevacizumab and temozolomide alter the patterns of failure in radiation treatment of glioblastoma multiforme", Radiation Oncology, 2013, vol. 8, No. 101, 7 pages.
Siebzehnrubl, Florian A. et al., "The ZEB1 pathway links glioblastoma initiation, invasion and chemoresistance", EMBO Mol Med, 2013, vol. 5, pp. 1196-1212.
Singh, Nidhi et al., "A combined ligand-based and target-based drug design approach for G-protein coupled receptors: application to salvinorin A, a selective kappa opioid receptor agonist", Comput Aided Mol Des, 2006, vol. 20, pp. 471-493.
Svetlov, Stanislav et al., "Lysophosphatidic Acid Induces Clonal Generation of Mouse Neurospheres via Proliferation of Sca-1- and AC133-Positive Neural Progenitors", Stem Cells and Development, 2004, vol. 13, pp. 685-693.
Svetlov, Stanislav et al., "Secretory PAF-acetylhydrolase of the rat hepatobiliary system: characterization and partial purification", the American Physiological Society, 1998, pp. G891-G900.
Svetlov, Stanislav et al., "Hepatic Regulation of Platelet-Activating Factor Acetylhydrolase and Lecithin:Cholesterol Acyltransferase Biliary and Plasma Output in Rats Exposed to Bacterial Lipopolysaccharide". Hepatology, 1999, vol. 30, No. 1, pp. 128-136.
Tabuchi, Sadaharu , "The autotaxin-lysophosphatidic acid-lysophosphatidic acid receptor cascade: proposal of a novel potential therapeutic target for treating glioblastoma multiforme", Health and Disease, 2015, vol. 14, No. 56, 9 pages.
Tomuleasa, C. et al., "Functional and molecular characterization of glioblastoma multiforme-derived cancer stem cells", Journal of BUON, 2010, vol. 15, pp. 583-591.
Van Brocklyn, James R., "Sphingolipid Signaling Pathways as Potential Therapeutic Targets in Gliomas", Mini-Reviews in Medicinal Chemistry, 2007,vol. 7, pp. 984-990.
Vescovi, Angello L. et al., "Brain tumour stem cells", Nature Reviews, Jun. 2006, vol. 6, pp. 425-436.
Villa, Salvador et al., "Radiation and concomitant chemotherapy for patients with glioblastoma multiforme", Chinese Journal of Cancer, 2014, vol. 33, issue 1, pp. 25-31.
Vuppala, Pradeep K. et al., "Development and validation of an UPLC-MS/MS method for the determination of 7-hydroxymitragynine, a µ-opioid agonist, in rat plasma and its application to a pharmacokinetic study", Biomed Chromatogr., Dec. 2013 , vol. 27, No. 12, pp. 1726-1732.
Wang, Fang et al., "Propranolol suppresses the proliferation and induces the apoptosis of liver cancer cells", Molecular Medicine Reports, 2018, vol. 17, pp. 5213-5221.
Wieland, Anja et al., "Anticancer Effects of Niclosamide in Human Glioblastoma", Clin Cancer Res., Aug. 1, 2013, vol. 19, No. 15, pp. 4124-4136.
Wong, Sophie Y. et al., "Constitutive activation of myosin-dependent contractility sensitizes glioma tumor-initiating cells to mechanical inputs and reduces tissue invasion", Cancer Res., Mar. 15, 2015, vol. 75, No. 6, pp. 1113-1122.
Wu, Miaojing et al., "Vincristine and temozolomide combined chemotherapy for the treatment of glioma: a comparison of solid lipid nanoparticles and nanostructured lipid carriers for dual drugs delivery", Drug Deliv, 2016, vol. 23, No. 8, pp. 2720-2725.
Yahyanejad, Sanaz et al., "An image guided small animal radiation therapy platform (SmART) to monitor glioblastoma progression and therapy response", Radiotherapy and Oncology, 2015, vol. 116, pp. 467-472.
Yekkirala, Ajay S. et al., "N-naphthoyl-β-naltrexamine (NNTA), a highly selective and potent activator of µ/κ-opioid heteromers", PNAS, Mar. 22, 2011, vol. 108, No. 12, pp. 5098-5103.
Young, Nicholas, et al., "Sphingosine-1-Phosphate Regulates Glioblastoma Cell Invasiveness Through the Urokinase Plasminogen Activator System and CCN1/Cyr61", Mol Cancer Res., Jan. 2009, vol. 7, No. 1, pp. 23-32.

* cited by examiner

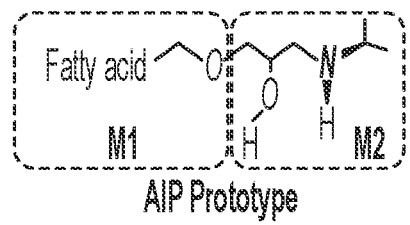
AIP Prototype
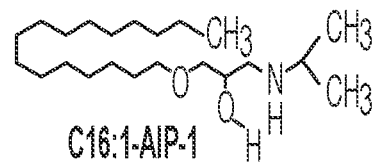
C16:1-AIP-1
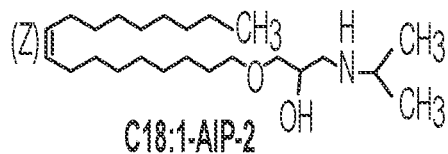
C18:1-AIP-2
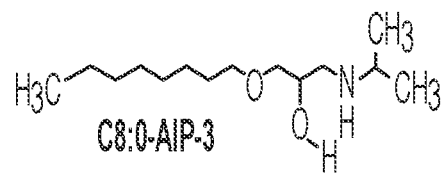
C8:0-AIP-3
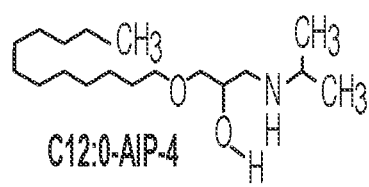
C12:0-AIP-4
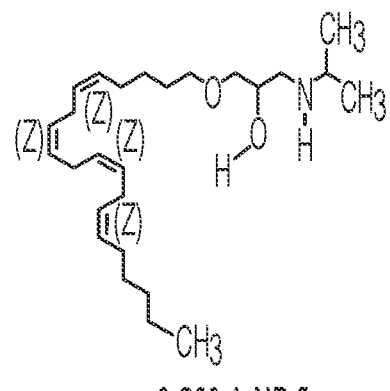
ω6-C20:4-AIP-5
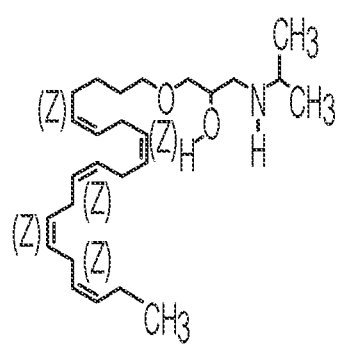
ω3-C20:5-AIP-6
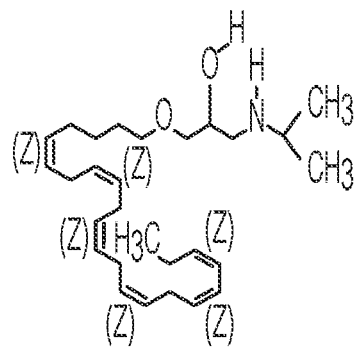
ω3-C22:6-AIP-7
FIG. 2

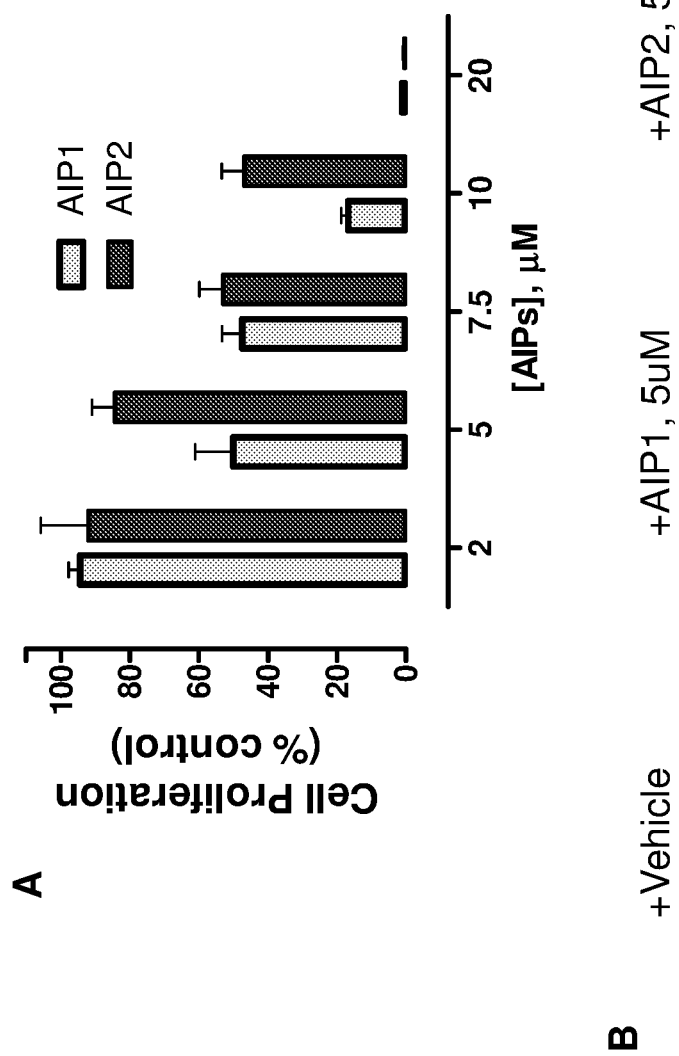
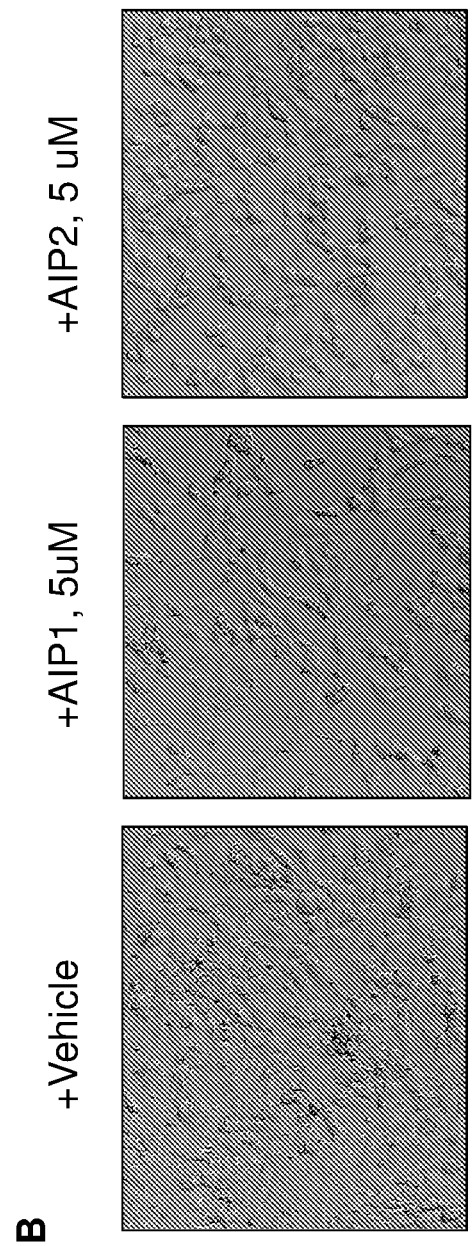
FIG. 10

COMPOSITIONS AND METHODS FOR TREATMENT OF CENTRAL NERVOUS SYSTEM TUMORS

CROSS-REFERENCE TO RELATED APPLICATIONS

This application claims the benefit of U.S. provisional application Ser. No. 62/534,992, filed 20 Jul. 2017 and U.S. provisional application Ser. No. 62/668,549, filed 8 May 2018. The entire contents of these applications are hereby incorporated by reference as if fully set forth herein.

BACKGROUND

Malignant glioblastoma and neuroblastoma are the most prevalent brain tumors with high mortality and recurrence rate and which lack efficient and safe treatments. About 23,770 new cases of brain cancer were diagnosed in 2016, with a relative 5-year survival prognosis of 33%. Malignant glioblastoma multiforme (GBM) remains the most prevalent brain tumor. The relapse of malignant glioblastoma after successful ablation is a significant problem. The major impediments for additional new drugs for treating brain tumors have been insufficient ability to cross blood-brain-barrier (BBB), low activity against silent cancer stem cells, and toxicity in the normal brain environment.

Currently approved drugs, such as Temozolomide or Carmustin, show some efficacy against certain glioblastoma types, but these compounds are non-specific, harmful for normal brain cells and do not prevent cancer recurrence from cancer stem cells. Despite the approval of several new drugs for its treatment (including temozolomide and the anti-VEGF monoclonal antibody, Bevacizumab), GBM patients generally develop frequent tumor relapses due to resistance of brain tumor-initiating stem-like cells and an impaired immune system after tumor ablation. The use of temozolomide resulted in a 2.5-month increase in overall survival and a 1.9-month increase in progression-free survival, relative to radiotherapy alone, but produced an increase in estimated cost-effectiveness ratios in 2013 from US$73,586 per quality-adjusted life-year to US$105,234. Hence, development of cost-efficient chemotherapy for preventing GBM recurrence would have significant impact on patient health care and market prospective. Long-term patient survival remains poor and there is a distinct need for new compounds and methods for treating brain tumors such as glioblastoma multiforme.

SUMMARY OF THE INVENTION

Patients with malignant glioblastoma multiforme (GBM) frequently develop tumor relapses due to survival of brain tumor-initiating cells and compromised immune system after tumor ablation and radiation treatment. Low brain bioavailability and toxicity to normal brain cells have also been major obstacles for drugs to aid preventing tumor re-growth.

The present invention relates to amphiphilic fatty acids, linked via either bond to a polar head of propranolol were synthesized to generate chimeric molecules (AIPs) with potent antitumor activity against human liver carcinoma cells. In the present application, data is presented showing that AIPs cross the blood-brain barrier and accumulate in brain, suppress activation of and destroy GBM tumor-initiating cells, and are non-toxic for normal brain cells. Therefore, these non-hydrolysable fatty acid ethers (AIPs) compounds can provide a new approach to chemotherapeutic treatment and prevention of recurrence of GBM, including concomitant treatment and prevention of recurrance.

The invention therefore relates to a compound of Formula I:

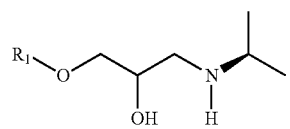

or a pharmaceutically acceptable salt thereof, wherein $R_1$ is an aliphatic chain having 6-30 carbon atoms that contains 0-6 unsaturations. Preferred compounds are those wherein the aliphatic chain is selected from the group consisting of C8:0, C12:0, C16:1, C18:1, C20:4, C20:5 and C22:6 carbon chains. For example compounds selected from the group consisting of

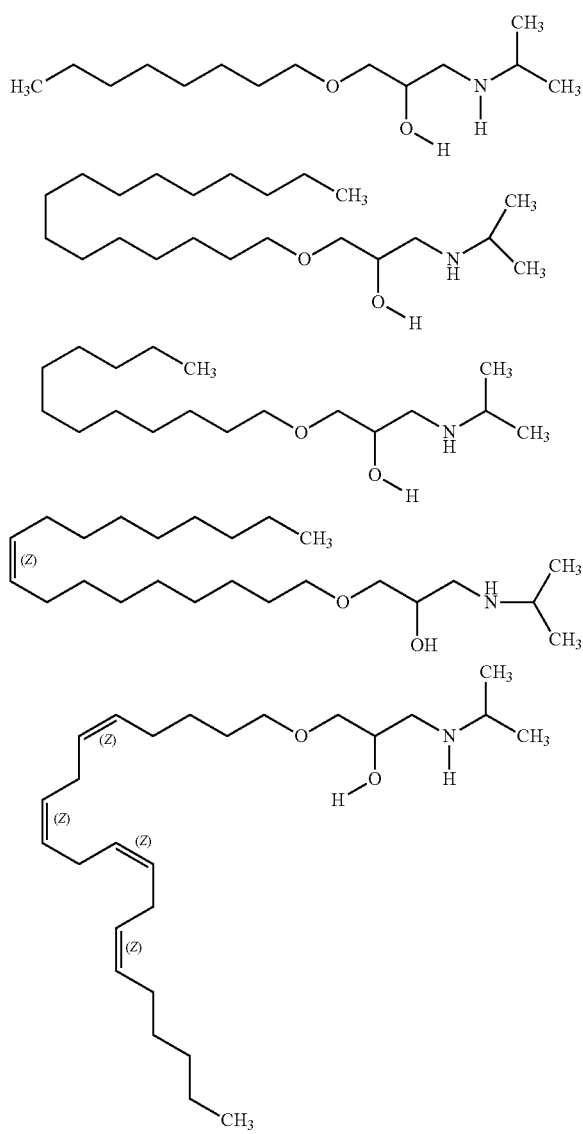

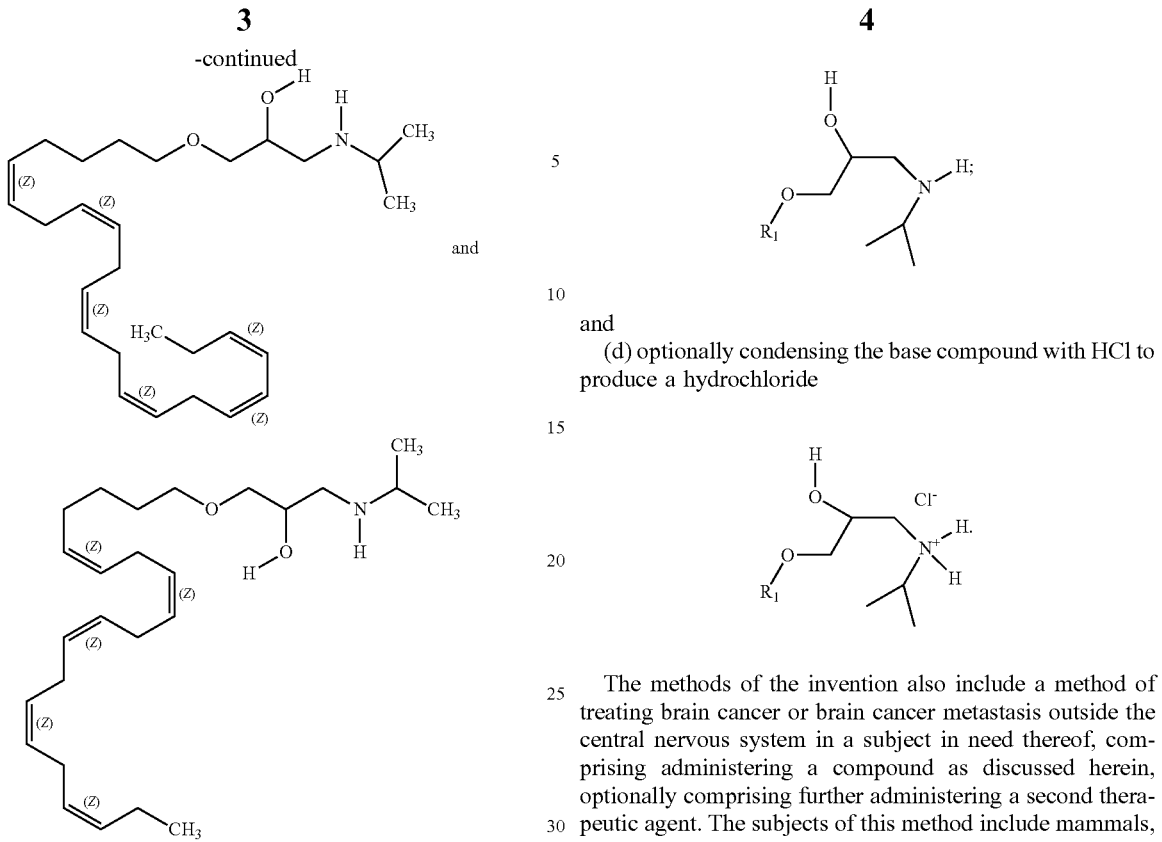

or a pharmaceutically acceptable salt thereof are preferred. A highly preferred compound contains a C18:1 fatty chain from omega-9 oleic acid.

The invention also contemplates pharmaceutical compositions comprising a pharmaceutically acceptable carrier and the compounds discussed herein or comprising a pharmaceutically acceptable carrier and one or more compounds of the compounds discussed herein. Preferred compositions contain a pharmaceutically acceptable carrier and one or more of the compounds according to the structures pictured above.

In addition, the invention provides a method of synthesizing the compound of claim 1, comprising the steps of:

(a) synthesizing a glycidyl ether fatty ether intermediate by mixing a fatty alcohol $R_1$—OH, wherein $R_1$ is an aliphatic chain having 6-30 carbon atoms that contains 0-6 double bonds, with glycidyl 4-toluenesulfonate (tosyl glycidol) in the presence of boron trifluoride diethyl etherate in anhydrous dichloromethane under an argon atmosphere to produce the intermediate

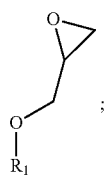

(b) purifying the intermediate;
(c) opening the glycidyl ring of the intermediate by stirring with isopropylamine in 2-propanol under an argon atmosphere to produce a 1-alkyl(alkenyl)oxy-3-isopropylamine-propan-2-ol base compound and
(d) optionally condensing the base compound with HCl to produce a hydrochloride The methods of the invention also include a method of treating brain cancer or brain cancer metastasis outside the central nervous system in a subject in need thereof, comprising administering a compound as discussed herein, optionally comprising further administering a second therapeutic agent. The subjects of this method include mammals, for example mammals selected from the group consisting of a human, a laboratory animal, a companion animal, and a livestock animal, and preferably a human.

Additional methods include a method of preventing recurrence of brain cancer or brain cancer metastasis outside the central nervous system after chemotherapy, surgery, or radiation therapy for brain cancer in a subject in need thereof, comprising administering a compound as discussed herein, a method of suppressing growth of brain cancer cells comprising administering a compound as discussed herein, a method of enhancing survival of normal central nervous system cells comprising administering a compound as discussed herein, and a method of improving recuperation from radiation, surgical or chemotherapy cancer treatment affecting the brain comprising administering a compound as discussed herein.

BRIEF DESCRIPTION OF THE DRAWINGS

The following drawings form part of the present specification and are included to further demonstrate certain embodiments of the present invention. The invention may be better understood by reference to one or more of these drawings in combination with the detailed description of specific embodiments presented herein.

FIG. 10A is a graph presenting data concerning cell viability/proliferation in adherent CA1 human glioblastoma multiforme cells, measured by MTS, added for an additional 2-3 hours. FIG. 10B is a set of microphotographs taken with a Hoffman modulation-equipped phase-contrast microscope at x20 magnification.

DETAILED DESCRIPTION

1. Definitions

Figure 1:
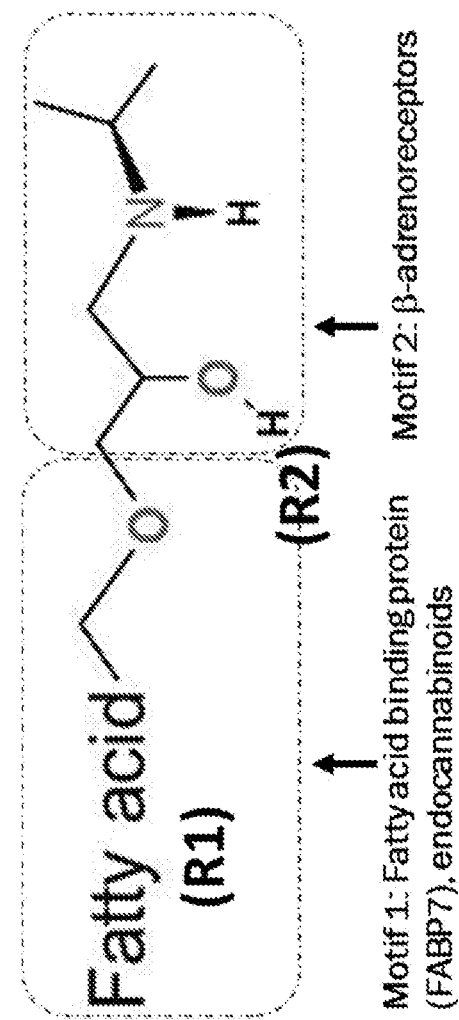
FIG. 1 shows the structural design of a brain cancer drug prototype: 1-alkyl(alkenyl)oxy-3-isopropylamine-propan-2-ol, collectively named AIPs, including the location of motifs 1 and 2. R1 contains C1-C30 saturated or unsaturated, linear or branched aliphatic chains; R2 contains H or a C1-C30 aliphatic chain.

Unless defined otherwise, all technical and scientific terms used herein have the same meaning as commonly understood by one of ordinary skill in the art. Although various methods and materials similar or equivalent to those described herein can be used in the practice or testing of the present invention, suitable methods and materials are described below. However, the skilled artisan understands that the methods and materials used and described are examples and may not be the only ones suitable for use in the invention. Moreover, as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary.

As used herein, the term "brain cancer" includes any tumor originating in the central nervous system, including the brain, spinal cord and retina, whether originating from neurons, glia, or any other cell present in the central nervous system. These cancers include, but are not limited to astrocytomas (e.g., pilocytic astrocytoma, diffuse astrocytoma, anaplastic astrocytoma, glioblastomas such as glioblastoma multiform, brainstem glioma, and the like), meningiomas, other gliomas (e.g., ependymomas, oligodendrogliomas, mixed gliomas, and the like), pituitary tumors, spinal cancer, cancer of the retina, and other brain tumors (e.g., craniopharyngiomas, germimomas, pineal region tumors, medulloblastomas, primary CNS lymphomas, and the like). The cancer can be grade I, grade II, grade III, grade IV, or metastatic brain cancer (cancers originating in another tissue but having spread to the brain, such as lung cancer, colon cancer, breast cancer, kidney cancer, and melanoma). Preferably, the brain cancer is glioblastoma multiforme, however any brain cancer is contemplated as part of the invention.

As used herein, the term "prevention" or "prevention of recurrence" refers to a reduction in the likelihood, frequency, and/or severity, of recurrence of the treated condition. Therefore, in populations of patients, prevention indicates that fewer treated patients will have a recurrence of disease, or the recurrence of disease will be less severe than in those patients treated with other or prior art methods.

As the term is used herein, a "subject in need" includes any animal, preferably a mammal, including mammals such as a human, a laboratory animal, a companion animal, and a livestock animal. Preferably, the subject is human, however the invention contemplates treatment of animals such as rats, mice and rabbits, livestock such as cattle, sheep, pigs and the like, and companion animals such as dogs, cats and other pets.

2. Overview

The brain is a lipid-rich organ, leading researchers to use natural and synthetic lipids in nanoparticles for targeted delivery of approved and experimental drugs for treatment of brain tumors to the brain. However, direct use of lipid molecules to target tumor-initiating stem cells for treatment and prevention of glioblastoma recurrence has not been known. Lipogenesis and signaling lipids fueling GBM growth such as sphingosine phosphate (S1P) or lysophosphatidic acid (LPA) have been proposed as targets, but not yet examined in preclinical and clinical studies. Stimulation of β-adrenoreceptors can promote glioblastoma cells proliferation. Re-purposing of the approved β-adrenoreceptor blocker propranolol has been implemented for treatment of melanoma, myeloma, breast and liver cancer. Any antitumor effects of propranolol appear to be mediated via downregulation of PI3K/Akt/VEGF pathways and involved β3-adrenoreceptor inhibition.

Therefore, the present invention involves a compound with a fatty alcohol moiety, attached by as an ether to a β-adrenergic antagonist core structure, which is useful for brain cancer treatment, prevention, and prevention of relapse, as an adjunct to brain cancer therapies of other types such as surgery, radiation, and chemotherapy, and for use with non-hyperproliferative brain and central nervous system cells as well.

4. Embodiments of the Invention

The compounds of this invention, referred to herein as AIPs, represent a new class of lipid molecules, in which fatty alcohols, including palmitic, oleic and other moieties, are linked via an ether bond to a polar head of β-adrenergic antagonists, for example the non-selective β-blocker, propranolol. AIPs structurally resemble competitive inhibitors of lysophospholipase D and sphingomyelin hydrolysis by sphingomyelinase. See FIG. 1, which shows a chemical drawing of an AIP prototype (Motif 1 is the fatty acid ether motif; Motif 2 is the β-adrenoreceptor antagonist motif). In this drawing, R1 indicates the "fatty acid" structure, by which is meant a long chain, for example C6 to C30 alkyl chain (an alkyl chain containing 6-30 carbon atoms). The alkyl chain can be C6, C8, C10, C12, C14, C16, C18, C20, C22, C24, C26, C28, or C30 in length, and can be saturated or unsaturated. It is contemplated that the fatty chain can contain 0, 1, 2, 3, 4, 5, 6, 7, or 8 unsaturations (double bonds), which can be configured in cis- or trans- positions, or both, within a single chain. In general, omega fatty alcohols are preferred, however this is not required. The standard nomenclature for such chains uses a C followed by an integer indicating the length of the chain in terms of the number of carbon atoms. Thus C18 refers to a straight chain alkyl moiety of 18 carbons. This is followed by a colon (:) and another integer, which indicates the number of unsaturations (double bonds) in the alkyl chain. Thus, for example, C20:0 refers to a 20-carbon alkyl chain with no double bonds and C16:4 refers to a 16-carbon alkyl chain with 4 double bonds, as is known by persons of skill in the art. The term "fatty" refers to the alkyl chain, so that a "fatty acid" is a long alkyl chain containing an acid, usually a terminal (or "omega") acid. A "fatty alcohol" refers to such a chain with an alcohol group.

Preferred compounds are those of Formula I:

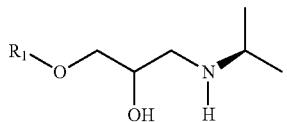

or a pharmaceutically acceptable salt thereof, wherein $R_1$ is an aliphatic chain having 6-30 carbon atoms that contains 0-6 unsaturations. See also FIG. 2 for exemplary structures, where, in the AIP Prototype structure, the term "fatty acid" indicates the aliphatic chain of a fatty acid rather than an acid-containing moiety attached at the point shown.

The AIP analogs are resistant to breakdown by common GI lipases, trypsin or brain fatty acid amidohydrolase (FAAH) for up to 24 hours at ambient temperature due to a linkage of fatty acid via ether bond (data not shown). AIP exhibit high GI absorption. A consensus LogP of 3.5-3.8 confirms AIPs' amphiphilic nature. Further, a lack of CYP450 inhibition and cardiotoxicity has been shown by evaluating by in silico using AIP screening against several available databases (e.g. SwissADME).

The tertiary amino group of AIPs allows formation of buffer-soluble salts suitable for oral administration, while the presence of lipophilic fatty acids facilitates nano-liposome formation and allows the compounds to be soluble in hydrophobic media. AIP-containing nanoparticles can be loaded with approved drugs (e.g. Temozolomide) and enhance efficacy and decrease toxicity like self-emulsifying drug delivery system. The simple yet flexible structural design and functional characteristics of AIPs assessed through in silico models and confirmed by experimental data, showed overall drug likeness. These allow the compounds to be formulated according to known methods as a pharmaceutical composition. Such pharmaceutical compositions are contemplated as part of the invention.

A procedure for chemical synthesis of AIPs was developed. The AIP compounds were synthesized and then validated by liquid chromatography-mass spectrometry (LC-MS), FIG. 3A and FIG. 3B, and tandem mass spectrometry, FIG. 4A and FIG. 4B. A glycidyl ether of the fatty alcohol intermediate was synthesized from the fatty alcohol and glycidyl 4-toluenesulfonate (tosyl glycidol) in the presence of boron trifluoride diethyl etherate. Then, an AIP base was prepared by opening the glycidyl ring with isopropylamine, and the AIP hydrochlorides were prepared by condensation of the AIP base with HCl in diethyl ether and dioxane. See example 1, below, for exemplary chemical methods.

The compounds of the invention include the base, and any pharmaceutically acceptable hydrate, solvate, acid or salt, and can be amorphous or in any crystalline form, or as an oil or wax. Any pharmaceutically acceptable salt can be used, as may be convenient. Generally, these salts are derived from pharmaceutically and biologically acceptable inorganic or organic acids and bases or metals. Examples of such salts include, but are not limited to: acetate, adipate, alginate, ammonium, aspartate, benzoate, benzenesulfonate (besylate), bicarbonate, bisulfate, butyrate, citrate, camphorate, camphorsulfonate, carbonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, magnesium, maleate, malonate, methanesulfonate (mesylate), 2-naphthalenesulfonate, nicotinate, nitrate, oxalate, palmoate, pectinate, persulfate, 3-phenylpropionate, phosphate, picrate, pivalate, potassium, propionate, salicylate, sodium, succinate, sulfate, tartrate, thiocyanate, toluenesulfonate (tosylate) and undecanoate salts.

The compounds also include any or all stereochemical forms of the therapeutic agents (i.e., the R and/or S configurations for each asymmetric center). Therefore, single enantiomers, racemic mixtures, and diastereomers of the therapeutic agents are within the scope of the invention. Also within the scope of the invention are steric isomers and positional isomers of the therapeutic agents. The therapeutic agents of some embodiments are also meant to include compounds which differ only in the presence of one or more isotopically enriched atoms. For example, therapeutic agents in which one or more atom is replaced by, for example, deuterium, tritium, $^{13}C$, $^{14}C$ (or any isotopic labels as commonly used in the art such as phosphorus, calcium, iodine, chlorine, bromine, or any other convenient element for isotopic labeling) are within the scope of this invention.

In a preferred method embodiments, the compounds described herein are formulated and are administered as a pharmaceutical composition that includes a pharmaceutically acceptable carrier and one or more pharmaceutical agent, including one or more of the inventive compounds described herein, and including one or more of the inventive compounds described herein with an additional agent, such as an anticancer drug of another class. A pharmaceutically acceptable carrier refers to any convenient compound or group of compounds that is not toxic and that does not destroy or significantly diminish the pharmacological activity of the therapeutic agent with which it is formulated. Such pharmaceutically acceptable carriers or vehicles encompass any of the standard pharmaceutically accepted solid, liquid, or gaseous carriers known in the art, such as those discussed in the art.

A suitable carrier depends on the route of administration contemplated for the pharmaceutical composition. Routes of administration are determined by the person of skill according to convenience, the health and condition of the subject to be treated, and the location and stage of the condition to be treated.

Such routes can be any route which the practitioner deems to be most effective or convenient using considerations such as the patient, the patient's general condition, and the specific condition to be treated. For example, routes of administration can include, but are not limited to: local or parenteral, including: oral, intravenous, intraarterial, intrathecal, subcutaneous, intradermal, intraperitoneal, rectal, vaginal, topical, nasal, local injection, buccal, transdermal, sublingual, inhalation, transmucosal, wound covering, direct injection into a tumor or the area surrounding a tumor, and the like. The administration can be given by transfusion or infusion, and can be administered by an implant, an implanted pump, or an external pump, or any device known in the art.

Therefore, the forms which the pharmaceutical composition can take will include, but are not limited to: tablets, capsules, caplets, lozenges, dragees, pills, granules, oral solutions, powders for dilution, powders for inhalation, vapors, gases, sterile solutions or other liquids for injection or infusion, transdermal patches, buccal patches, inserts and implants, rectal suppositories, vaginal suppositories, creams, lotions, oils, ointments, topical coverings (e.g., would coverings and bandages), suspensions, emulsions, lipid vesicles, and the like.

Treatment regimens include a single administration or a course of administrations lasting two or more days, including a week, two weeks, several weeks, a month, two months, several months, a year, or more, including administration for the remainder of the subject's life. The regimen can include multiple doses per day, one dose per day or per week, for example, or a long infusion administration lasting for an hour, multiple hours, a full day, or longer.

Dosage amounts per administration include any amount determined by the practitioner, and will depend on the size of the subject to be treated, the state of the health of the subject, the route of administration, the condition to be treated or prevented, and the like. In general, it is contemplated that for the majority of subjects, a dose in the range of about 0.01 mg/kg to about 100 mg/kg is suitable, preferably about 0.1 mg/kg to about 50 mg/kg, more preferably about 0.1 mg/kg to about 10 mg/kg, and most preferably about 0.2 mg/kg to about 5 mg/kg are useful. This dose can be administered weekly, daily, or multiple times per day. A dose of about 0.1 mg, 0.2 mg, 0.25 mg, 0.5 mg, 1 mg, 5 mg, 10 mg, 20 mg, 40 mg, 80 mg, 100 mg, 250 mg, 500 mg, or 1000 mg can be administered.

Any pharmaceutically acceptable carrier is contemplated for use with the invention, such as the carriers and excipients known in the art. Carriers can include, for example, starch (e.g., corn starch, potato starch, rice starch), celluloses (e.g., microcrystalline cellulose, methylcellulose, and the like), sugars (e.g., lactose, sucrose, glucose, fructose, and the like), clays, minerals (e.g., talc, and the like), gums, flavorings, preservatives, colorings, taste-masking agents, sweeteners, gels, waxes, lipids (e.g., lipid vesicles or nanoparticles), oils, polyethylene glycols, glycerine, propylene glycol, solvents (e.g., water or pharmaceutically acceptable organic solvents), saline solutions (e.g., saline solutions, electrolyte solutions, lactated saline solutions, and the like), emulsifiers, suspending agents, wetting agents, fillers, adjuvants, dispersants, binders, pH adjusters and buffers, antibacterial agents (e.g., benzyl alcohol, methyl parabens, and the like), antioxidants (e.g., ascorbic acid, sodium bisulfite, and the like), chelating agents (e.g., EDTA and the like), glidants (e.g., colloidal silicon dioxide), and lubricants (e.g., magnesium stearate and the like). The compounds or pharmaceutical compositions containing the compounds can be provided in containers such as ampoules, bottles, pre-filled syringes, and the like. Extended and sustained release compositions also are contemplated for use with and in the inventive embodiments. Thus, suitable carriers can include any of the known ingredients to achieve a delayed release, extended release or sustained release of the active components. Preferably, the pharmaceutical compositions comprise a therapeutically effective amount.

The compounds of the invention are non-hydrolysable fatty acid ethers, linked to a β-adrenoreceptor blocker, and are amphiphilic molecules. Experimental data have shown that AIPs cross the blood-brain barrier in vivo. The compounds contain endocannabinoid/fatty acid motifs linked to a beta-adrenoreceptor antagonist motif in one molecule (see FIG. 1 and FIG. 2).

Endocannabinoids are endogenous, lipid-based retrograde neurotransmitters that bind to cannabinoid receptors (CB1 and CB2). These receptors are found in the central and peripheral nervous systems and regulate processes including cognition, appetite, memory, and mediate the pharmacological effects of cannabis. Any fatty chain that binds to cannabinoid receptors is contemplated for use in the invention, including chains of diverse lengths, saturated or unsaturated. Preferably, the total length of the carbon chains attached to the ether linkage are in the range of 6-30 carbon atoms or 12 to 22 carbon atoms, more preferably in the range of 16 to 20 carbon atoms. The aliphatic chain can be saturated, but preferably the chain is unsaturated. Preferred compounds have 1 to 6 double bonds, or more preferably 1 to 5 double bonds, which preferably are located at the ω3 position.

The beta-adrenergic antagonist or blocker motif of preferred compounds is shown in FIG. 1, and is shown as the right side of the structure of propranolol, below, an exemplary "beta-blocker" drug. Known beta-adrenergic antagonists include Acebutolol, Atenolol, Betaxolol, Bisoprolol, Bucindolol, Carvedilol, Celiprolol, Dichloroisoprenaline, Esmolol, Labetalol, Metoprolol, Nebivolol, Oxyprenolol, Penbutolol, Pindolol, Propranolol, Sotalol, and Timolol.

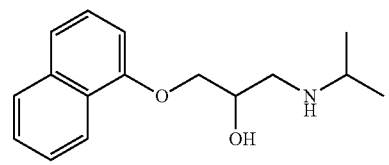

Propranolol

Predicted and confirmed targets of the inventive compounds include the brain isoform of fatty acid binding protein (FABP7), fatty acid receptors GPR40, endocannabinoid receptor CB1, and β-adrenoreceptors. AIPs inhibited β1- and β3-adrenoreceptors (β-ADR), strongly suppressed phosphoinositide-dependent kinase-1/phosphoinositide 3-kinase/protein kinase B (PDK1/P13K/Akt), activated (PTEN) phosphorylation, and promoted cancer cell death via caspase-3 and caspase-7 and LC3-mediated autophagy. The threshold toxicity for normal human hepatocytes was shown to be much greater (>7 times) than the IC50 for hepatoma.

Figure 5:
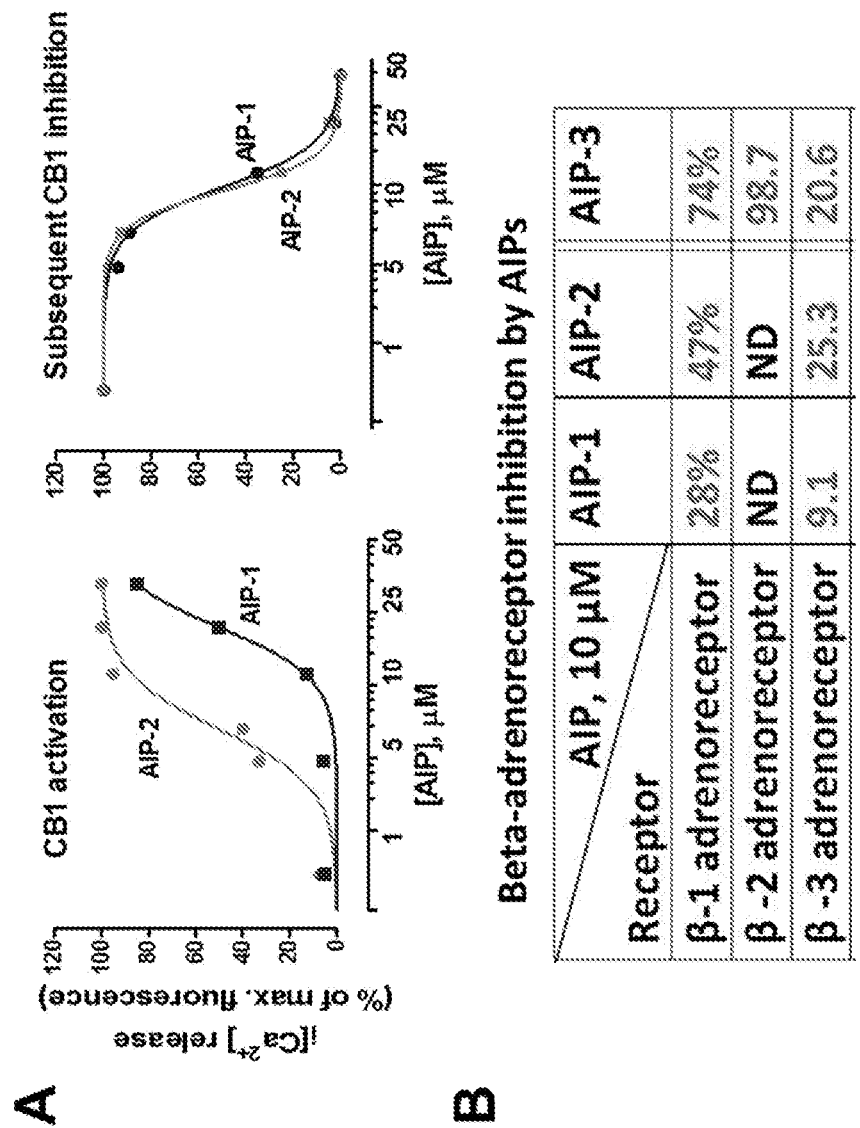
FIG. 5A shows $Ca^{2+}$ mobilization by AIPs in CHO cells overexpressing CB1 receptor followed by inhibition of calcium responses to CP55,940.
FIG. 5B presents data demonstrating that AIPs inhibit beta-adrenoreceptor activation by isoprenaline in CHO cells overexpressing ADR.

FABP7 is expressed predominantly in immature glia and in glioblastoma cells; CB1 and β-ADR are expressed predominantly in neuronal cells. AIP dose-dependently activates the CB1 receptor in CHO cells overexpressing CB1, followed by subsequent suppression of CP55,940 CB1 agonist stimulation (see FIG. 5A). Without wishing to be bound by theory, it is possible that AIPs inhibit the S-palmitoylation profile by DHHC palmitoyl transferases (PAT), specifically ZDHHC15 and ZDHHC5 which are up-regulated as drivers of cancer cell survival in p53-mutant malignant glioma cells. AIPs also inhibit β-adrenergic calcium mobilization by isoprenaline (FIG. 5B) and therefore are active at β-adrenergic receptors.

Figure 7:
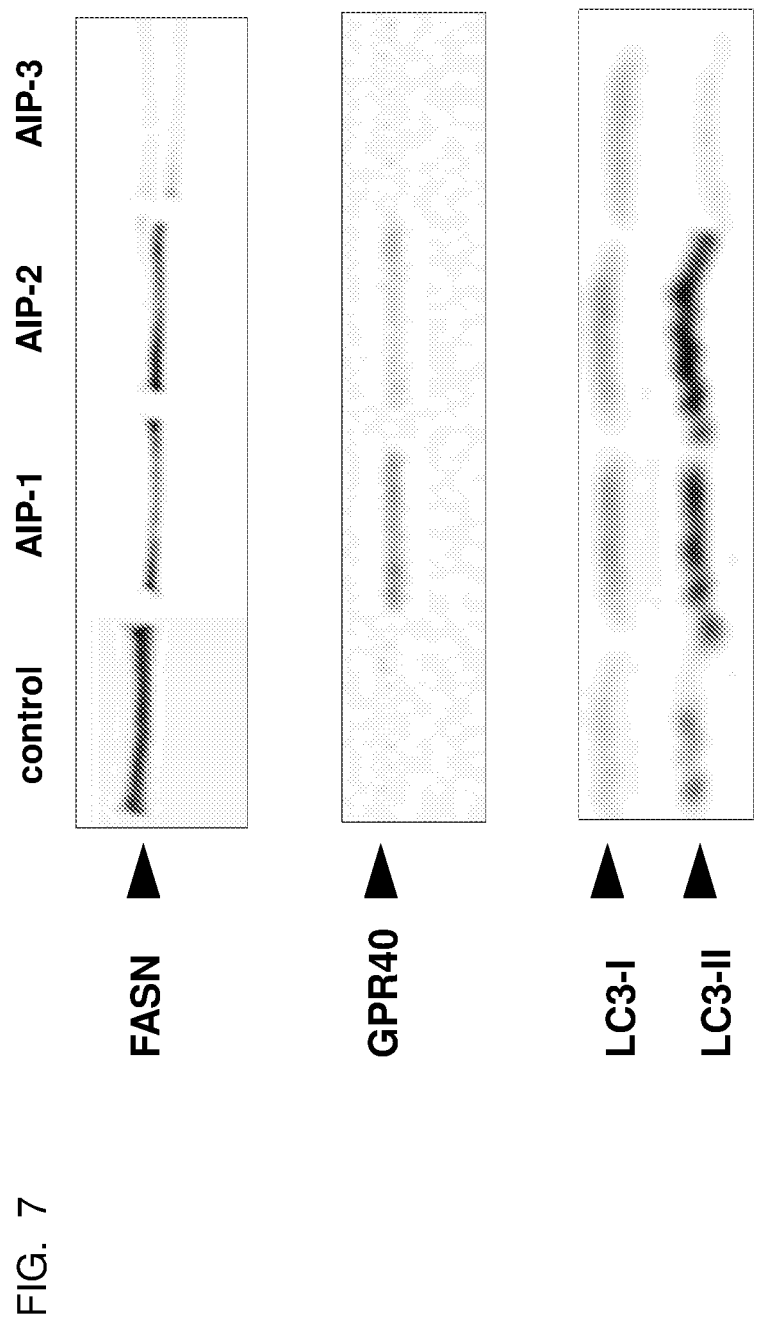
FIG. 7 presents data showing that treatment with AIPs (10 μM for 24 hours) suppressed expression of FASN, upregulated GPR40, and stimulated autophagy in human carcinoma HUH-7 cells.
Figure 8:
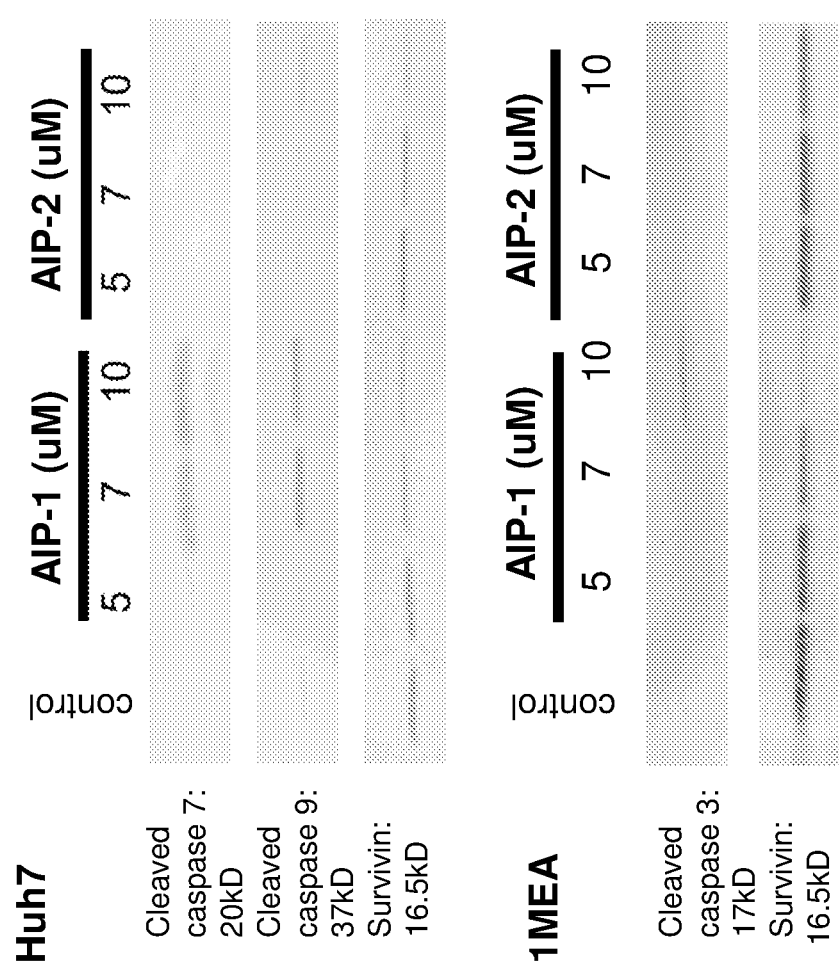
FIG. 8 presents data showing that treatment with AIPs (10 μM for 24 hours) suppressed expression of caspases, and stimulated apoptosis and autophagy in human carcinoma HUH-7 cells and mouse hepatoma cells, 1MEA.
Figure 9:
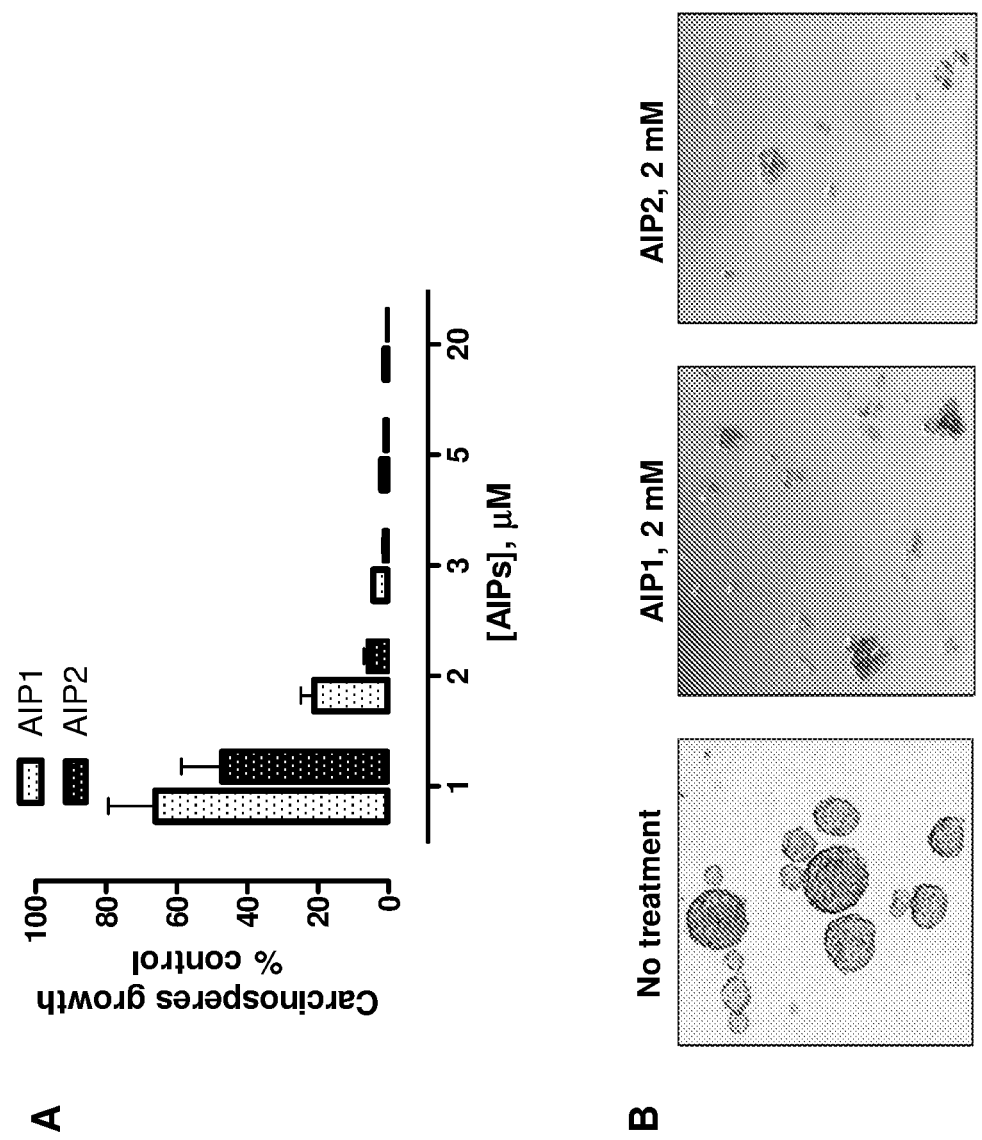
FIG. 9A is a graph presenting data showing that AIPs block development of brain tumor-initiating stem cells. IC50: 1.73 μM AIP1; IC50: 1.1 μM AIP2.
FIG. 9B is a set of representative photographs of the cells treated as indicated.

AIPs at 10 µM concentration suppressed basal phosphorylation of AKT in human hepatocarcinoma (HUH-7) cells (FIG. 6), suppressed expression of FASN, up-regulated GPR40, and stimulated autophagy in HUH-7 cells (FIG. 7), and suppressed expression of caspases, stimulating apoptosis and autophagy in those same cells (FIG. 8). Further, AIPs blocked a formation and growth of CA1 cancer stem cell-derived carcinoid bodies ('carcinospheres') in a dose-dependent manner with a greater potency than for bulk growing cells and IC50 of 1.7 µM for AIP1 and 1.1 µM for AIP2 (FIG. 9A and FIG. 9B). The AIPs abolished activation and growth of stem cell carcinospheres at concentrations 5 µM and higher (FIG. 9). An advantageous characteristic of the AIP compounds described here therefore is a strong inhibition of brain tumor-initiating 'cancer stem cells,' with an IC50 of 1.65 µM for AIP1 and 1.1 µM for AIP2. This is much lower than for proliferating glioblastoma cells, which have an IC50 of 5.9 and 7.1 µM, respectively (Compare data in FIG. 9 and FIG. 10A). AIPs suppressed growth and survival of human malignant glioblastoma cells (CA1) in a dose-dependent manner with IC50 of 5.1 µM for AIP1 and 6.9 µM for AIP2 (FIG. 10A and FIG. 10B). AIP1 and AIP2 destroyed all cancer cells and nearly wiped out a cell monolayer at concentrations of 20 µM (FIG. 10). These data show that the compounds can be effective in treating and preventing relapse of cancers such as glioblastoma multiforme.

Figure 11:
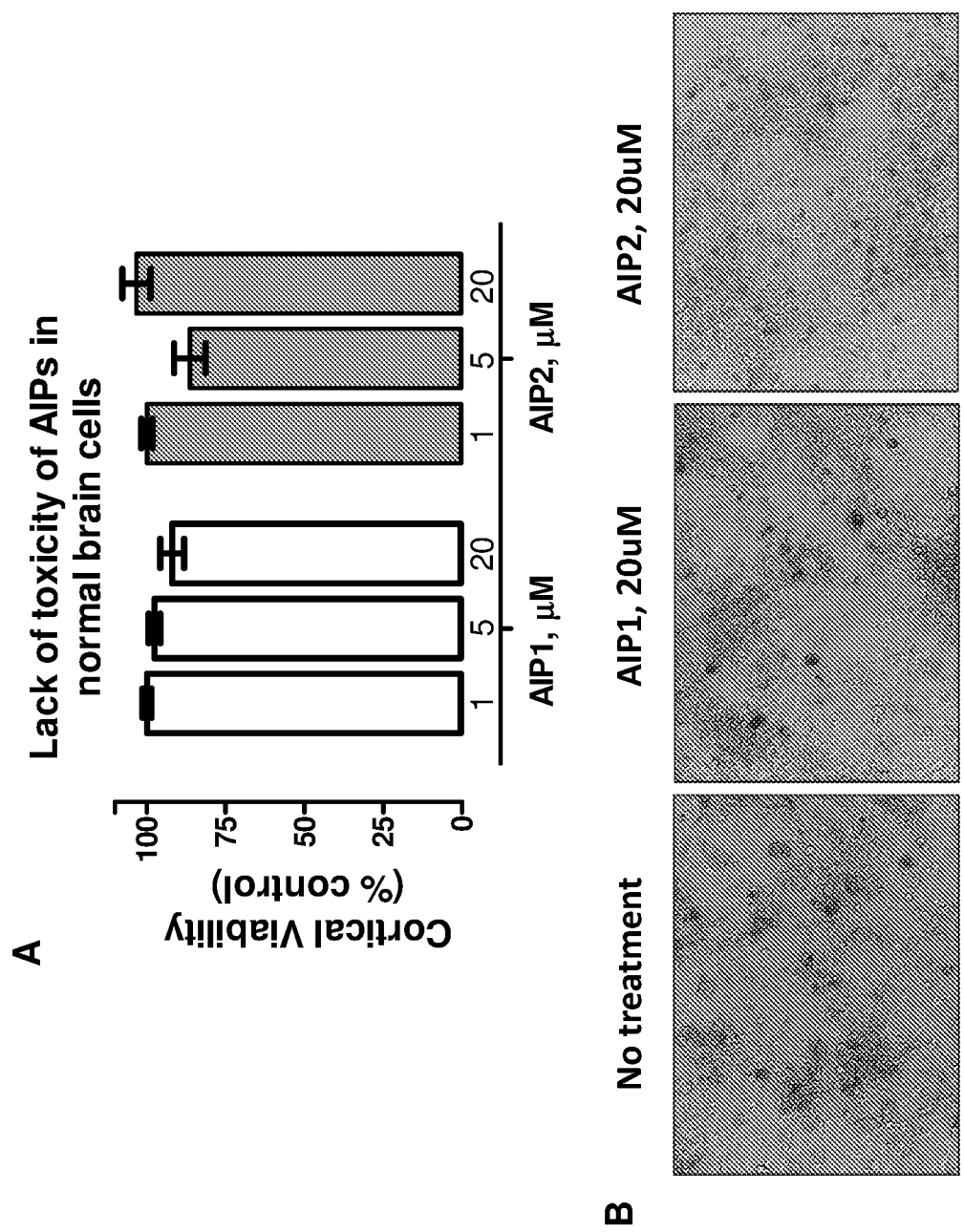
FIG. 11A is a graph showing cell viability of normal cortical cells treated with up to 20 μM concentrations of AIP1 and AIP2, as indicated.
FIG. 11B is a set of photomicrographs showing the cells.

Safety of AIPs has been ascertained using rat primary cortical cultures composed of glia and neurons. In mixed cortical cultures, AIPs were not cytotoxic and did not affect normal cell viability and survival at concentrations of up to 20 µM (FIG. 11A). The cell integrity and structural architecture were not altered following incubation with AIPs for a week (FIG. 11B). Cell cultures can be treated at 3 days after plating with 10 µM of cytosine arabinoside for 2 days to obtain neuron-enriched cell population for testing with AIP. The MTS CellTiter 96® aqueous test can be used for analysis of metabolic stability and LDH release for cell toxicity. Cell integrity and tight junctions can be determined by connexin 43 expression.

Figure 12:
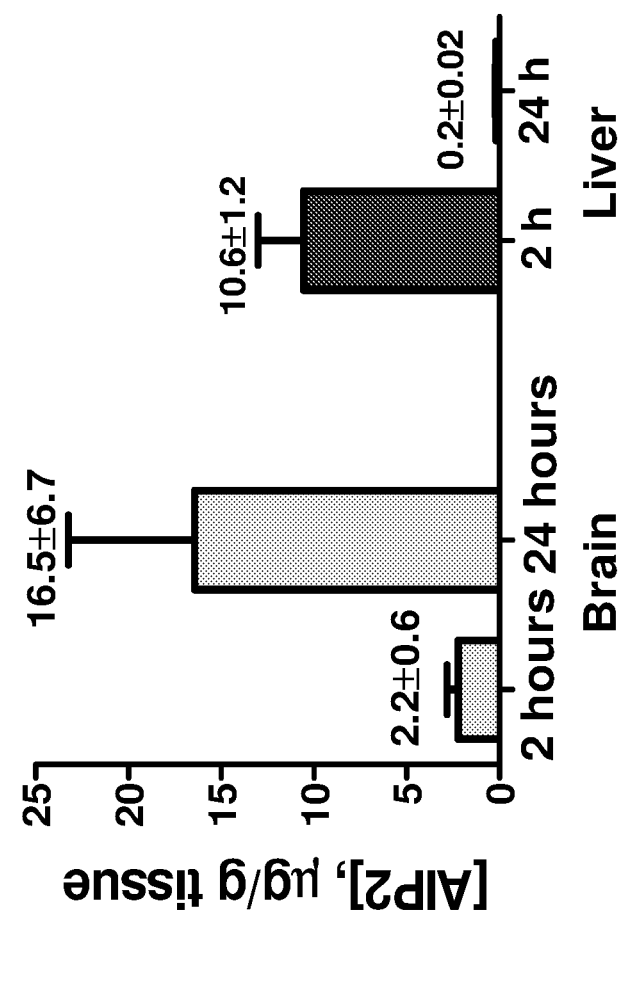
FIG. 12A shows tissue accumulation of AIP2 after intraperitoneal injection of 2 mg in mice, as determined by C8-HPLC and estimated by nano-LC-MSMS.
FIG. 12B presents data from an LC-mass spectrometry analysis of AIP2 in brain 24 hours after AIP2 injection.
Figure 12B:
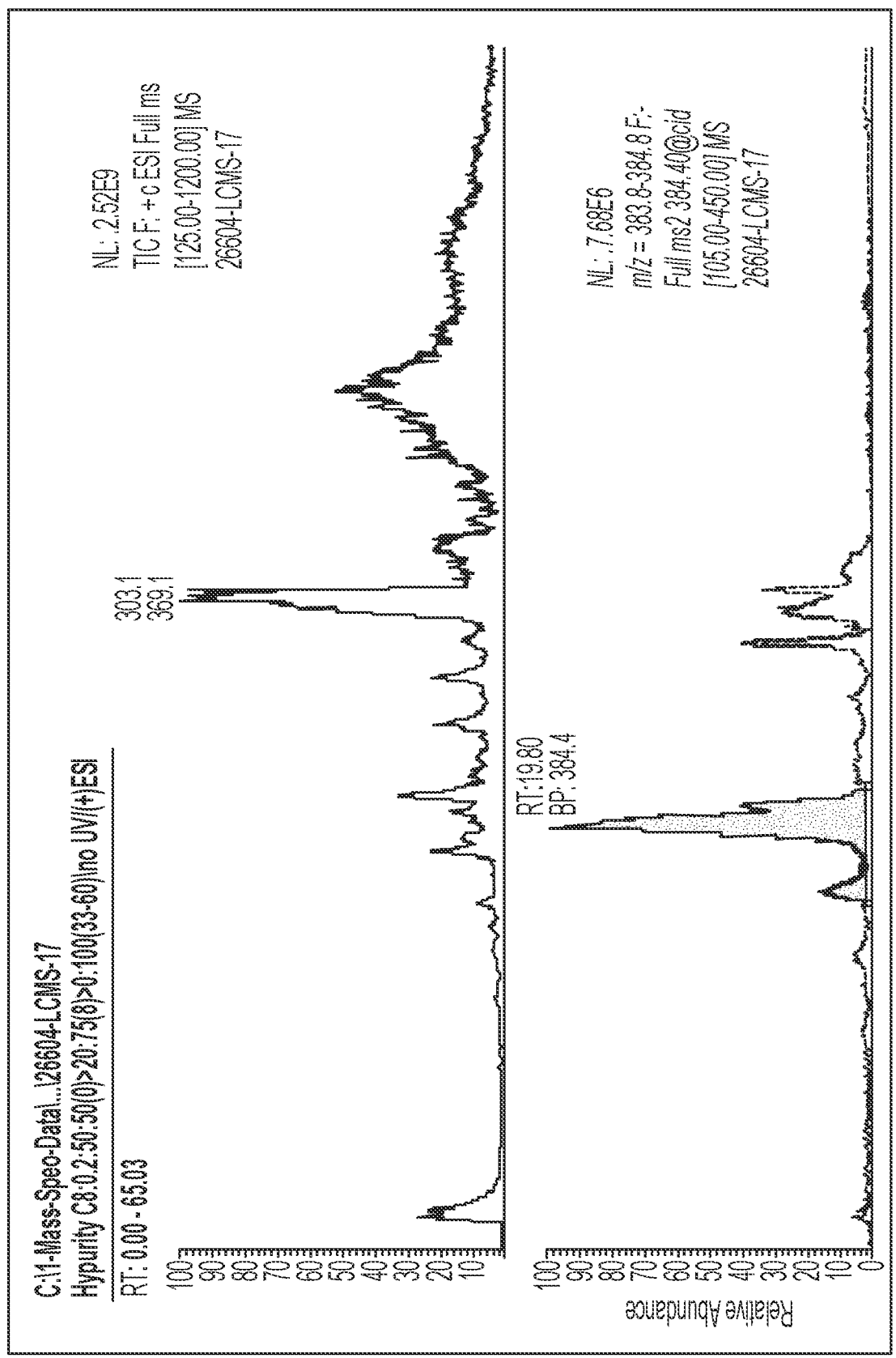

Non-metabolized AIP2 analog accumulated in brain and liver in a time-dependent fashion, indicating significant blood-brain-barrier (BBB) penetration and brain accessibility 24 hours after intraperitoneal injection. See FIG. 12A and FIG. 12B. Thus, AIPs completely abolished proliferation and destroyed adherent human glioblastoma cells at 20 µM, but did not affect the viability of primary cortical cultures at this concentration. AIPs demonstrate high bioavailability score of 0.55, drug likeness and BBB+using in silico software analyses (data not shown). These data show that the inventive compounds can access tumors in the brain after systemic administration and can be used safely without toxicity to normal brain cells.

In summary, advantageous AIP features include: (a) suppression of tumor-initiating cancer stem cells with an IC50 much lower than for toxicity for normal cortical cells; (b) suppression of adherent glioblastoma proliferation in culture; (c) blood-brain barrier permeability, GI adsorption and overall drug-like functional characteristics; (d) safety for normal brain cells and human hepatocytes, in particular compared to the existing treatment, Temazolomide; (e) targets including PDK1/AKT pathways, β-adrenoreceptors and fatty acid metabolism/signaling; and (f) cost-effective production. These characteristics render AIPs as an excellent platform for drug development suitable for prevention of glioblastoma recurrence. The data presented here establish the efficacy of AIPs to block glioblastoma tumor initiating cells and suppress intracranial tumor formation, as well as reduce tumor recurrence. Therefore, the inventive AIP technology possesses a high rates of blood-brain-barrier permeabilization and minimal side effects on normal tissues, as well as definite pharmacologic effects, producing a pharmacological tool for treatment and prevention of relapse of brain tumors.

The present invention includes a method of treating brain cancer or brain cancer metastasis outside the central nervous system in a subject in need thereof, comprising administering an AIP compound as described here, either alone as a monotherapy, or in conjunction or combination with a second therapeutic agent or method. The inventive methods can be used simultaneously or sequentially (before, after, or both) with other cancer treatments, including drug/chemotherapy treatments, surgery, and radiation, as are known in the art.

The inventive compounds are given to a subject in need at doses and according to treatment regimens that are determined by a person of skill in the art. A subject in need is a mammal that has been diagnosed with a brain cancer, for example glioblastoma multiforme, or is at risk for such a brain cancer, and includes human patients. The contemplated subjects include those who have been treated for a brain cancer of any stage, including metastasized brain cancers, recently or in the past, since such subjects may be susceptible to relapse of the disease, and includes both patients for whom an initial treatment has not been successful in achieving remission and those for whom it has. Therefore, the inventive methods include a method of preventing recurrence of brain cancer or brain cancer metastasis outside the central nervous system after chemotherapy, surgery, or radiation therapy for brain cancer in a subject in need thereof, by administering a compound as described herein. The invention also includes a method of suppressing growth of brain cancer cells comprising administering these compounds.

Further, the inventive methods include a method of improving recuperation from radiation, surgical or chemotherapy cancer treatment affecting the brain, by administering an inventive compound as described herein. The invention also includes a method of enhancing survival of normal central nervous system cells comprising administering a compound as described herein.

5. Examples

This invention is not limited to the particular processes, compositions, or methodologies described, as these may vary. The terminology used in the description is for the purpose of describing the particular versions or embodiments only, and is not intended to limit the scope of the present invention which will be limited only by the appended claims. Although any methods and materials similar or equivalent to those described herein can be used in the practice or testing of embodiments of the present invention, the preferred methods, devices, and materials are now described. All publications mentioned herein, are incorporated by reference in their entirety. Nothing herein is to be construed as an admission that the invention is not entitled to antedate such disclosure by virtue of prior invention.

Example 1. General Methods

A. Chemistry and AIP Analogs.

AIP hydrochlorides containing different fatty acid chains, for example, C16:0-AIP1, C18:1-AIP2, and C8:0-AIP3, have been synthesized at ALCHEM QC/QA-controlled and FDA-certified facilities and validated for chemical ID and purity (>95%) by Liquid Chromatography/Mass Spectrometry and NMR as described previously. Additional AIPs can be produced according to a modified scheme with glycidyl 4-toluenesulfonate and boron trifluoride etherate instead of epichlorhydrin to avoid safety issues (ALCHEM SOP). If necessary, due to poor initial solubility of AIP hydrochloride in PBS, pH 6.8 (40° C.), 2% polyvinyl pyrrolidone (PVP) in vehicle can be added to enhance AIP solubilization.

Figure 3A:
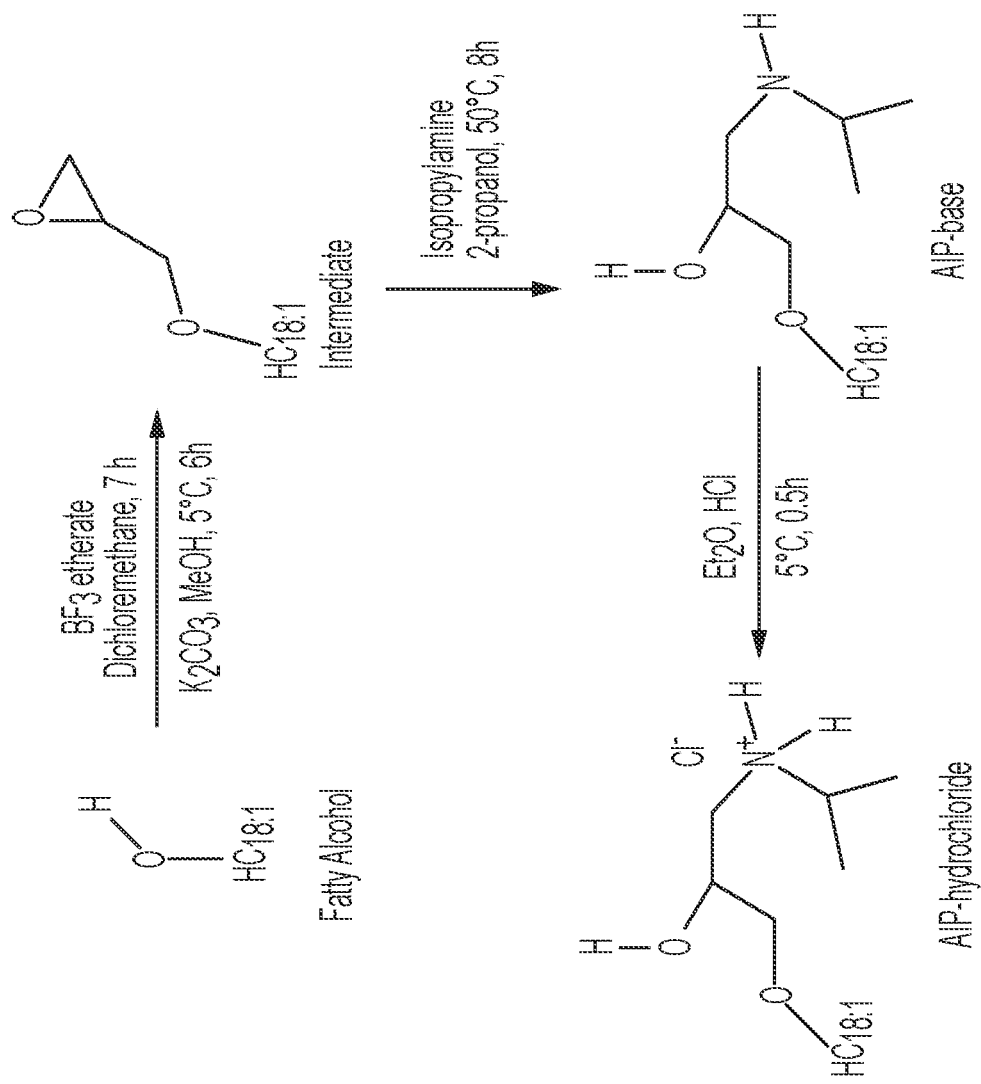
FIG. 3A is a schematic presentation of the chemical synthesis of AIP analogs.
Figures 1, 3B:
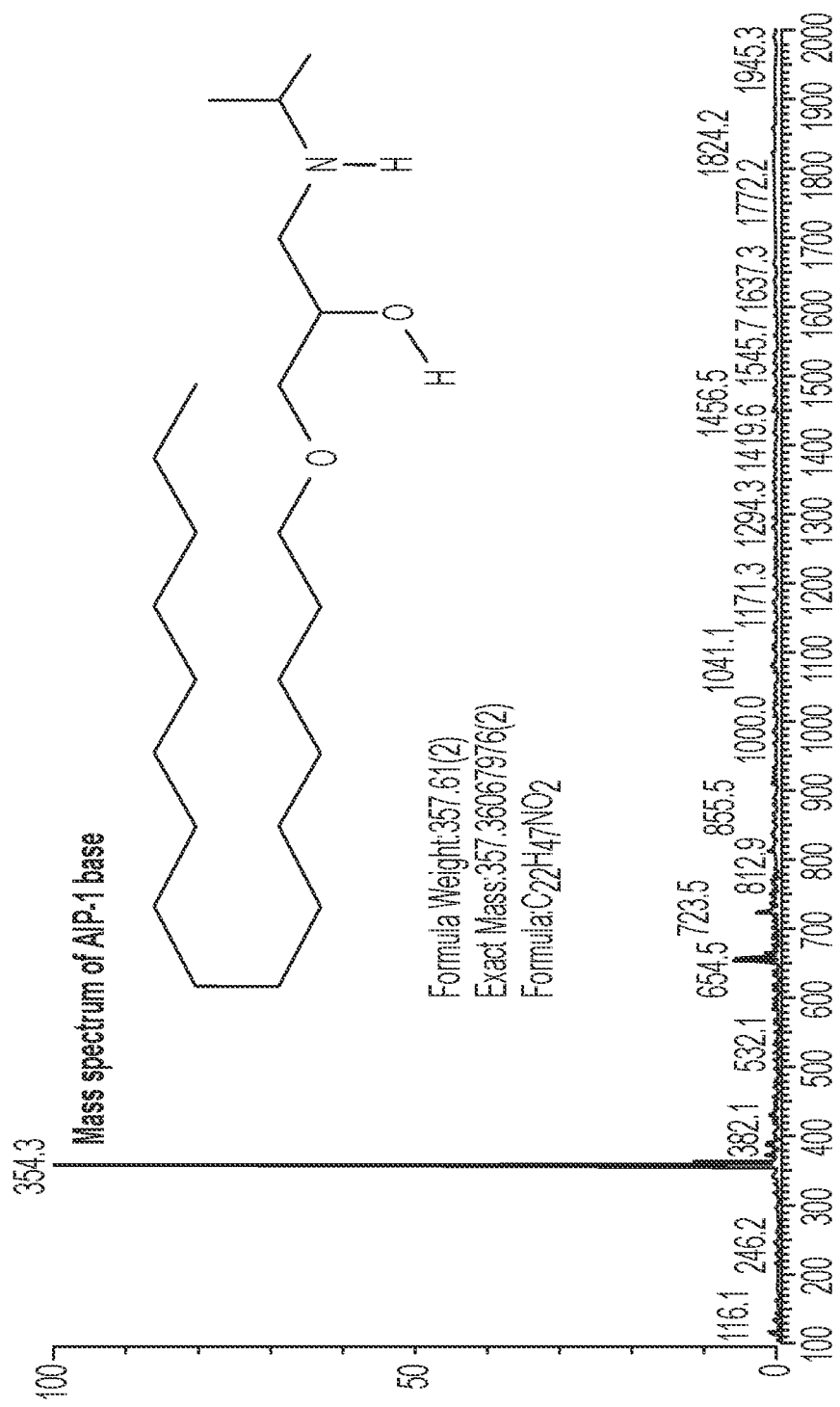
FIG. 3B shows mass spectrometry validation of AIP1 and AIP2 analogs.
Figures 2, 3B:
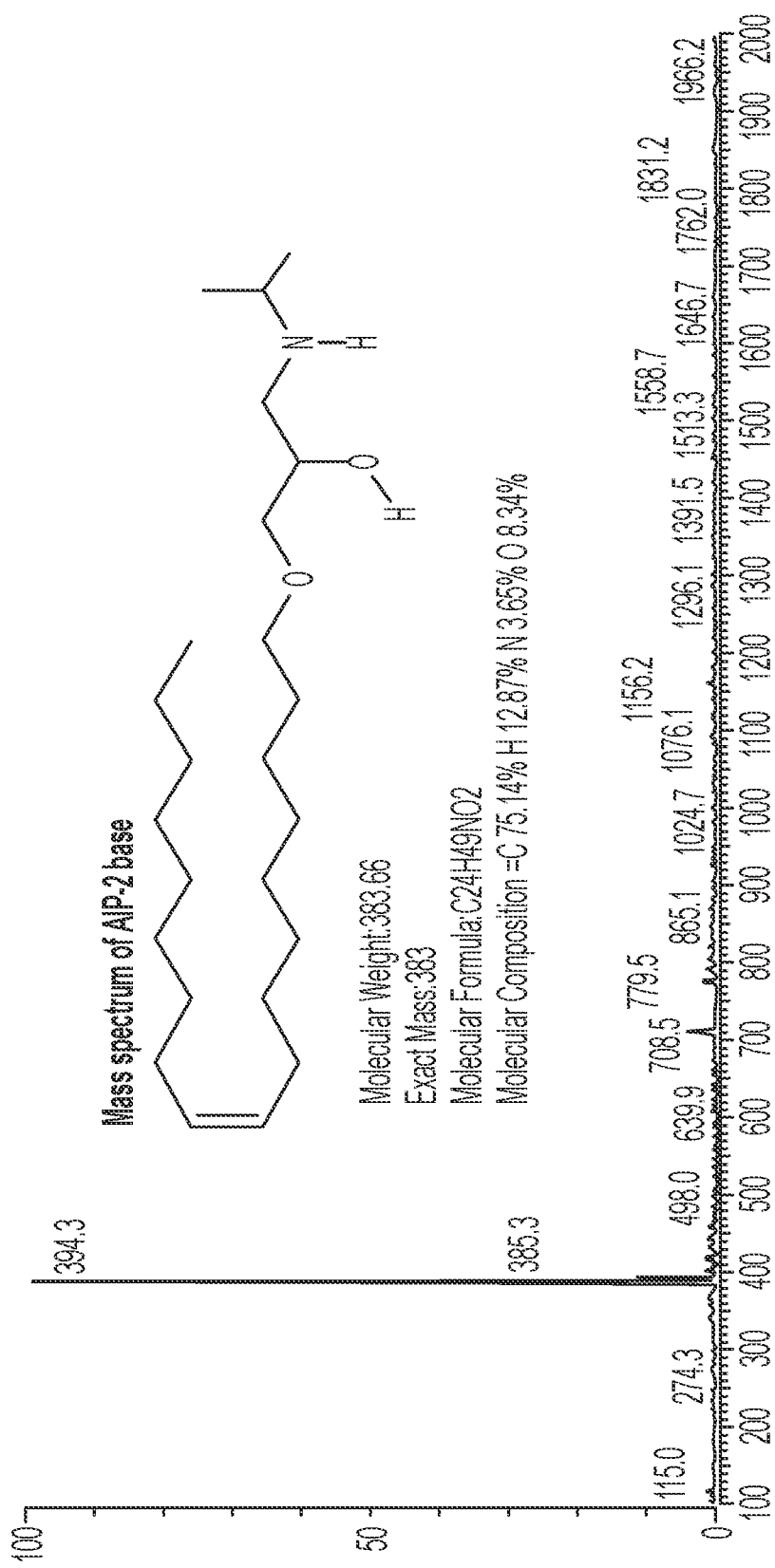
FIG. 2 shows the chemical structure of the AIP prototype and seven AIP analogs useful for treatment of brain cancer.
Figures 4A, 4B:
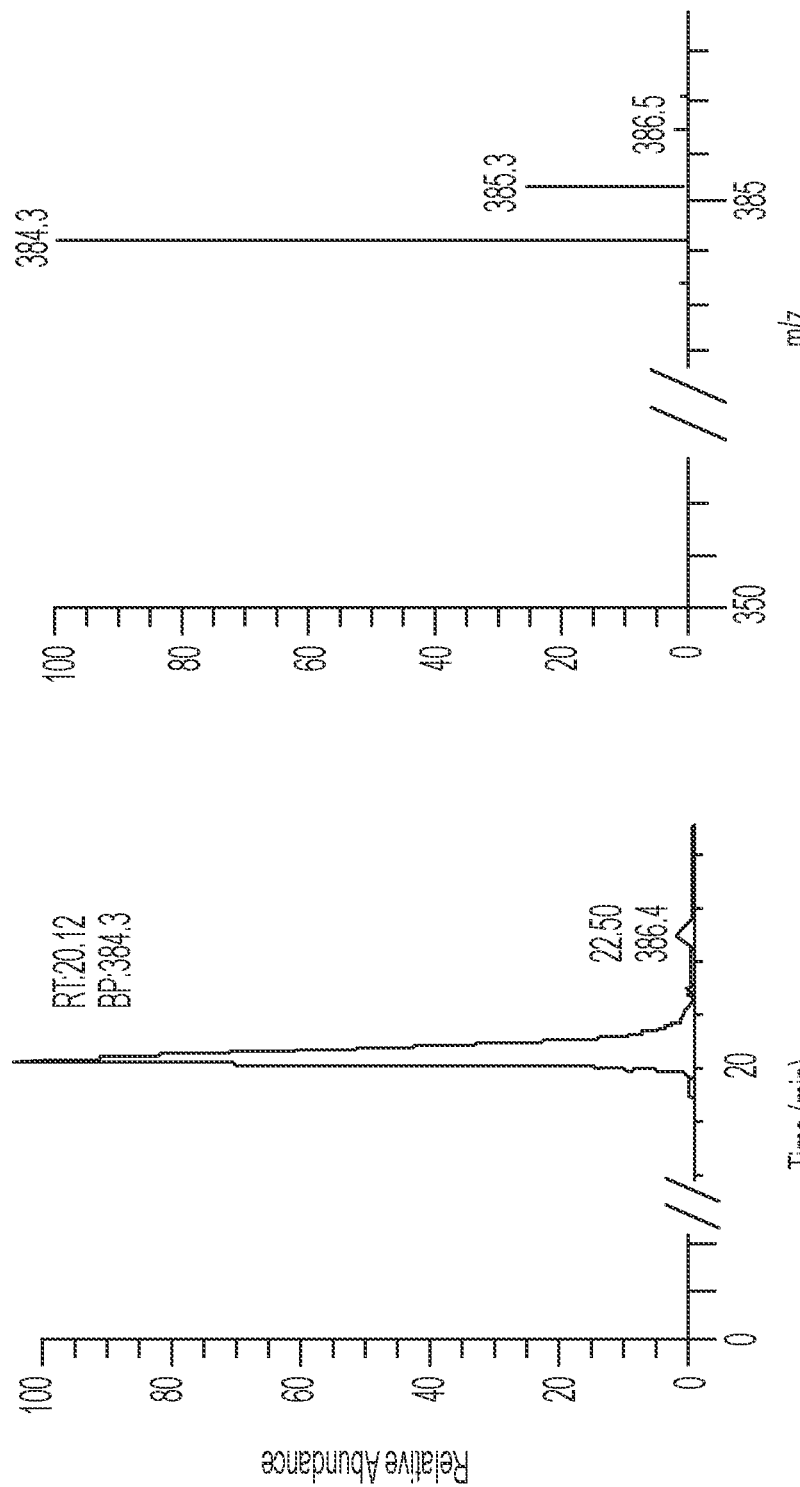
FIG. 4A and FIG. 4B show validation of AIP1 and AIP2 by tandem mass spectrometry. See FIG. 3A for the chemical synthesis.

See FIG. 3A for chemical synthesis of AIP analogs and FIG. 3B for exemplary validation by electrospray ionization-tandem mass spectrometry of AIP2. The general synthetic method is completed by (a) synthesizing a glycidyl ether fatty ether intermediate by mixing a fatty alcohol

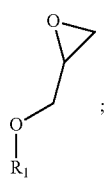

wherein R1 is an aliphatic chain having 6-30 carbon atoms that contains 0-6 double bonds, with tosyl glycidol in the presence of boron trifluoride diethyl etherate in dichloromethane for 7 hours to produce the intermediate

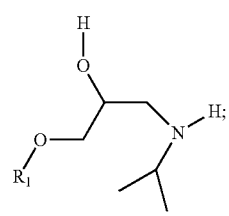

(b) opening the glycidyl ring of the intermediate by mixing with isopropylamine in 2-propanol at 50° C. for 8 hours to produce a 1-alkyl(alkenyl)oxy-3-isopropylamine-propan-2-ol base compound

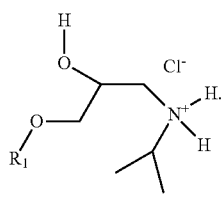

and (d) optionally condensing the base compound with HCl in diethyl ether and dioxane at 5° C. for 5 hours to produce a salt

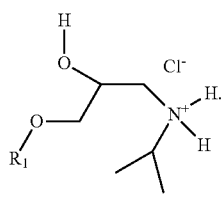

Because unsaturated AIP can be susceptible to oxidation and degradation, synthesis of AIP should be performed under argon atmosphere, when necessary.

1H NMR (300 MHz, DMSO-d6): δ 8.92 (br s, 1H), 8.51 (br s, 1H), 5.56 (d, 1H, J=4.8 Hz), 5.30 (t, J=4.5 Hz, 2H), 4.02-3.80 (m, 1H), 3.40-3.26 (m, 5H), 3.00-2.90 (m, 1H), 2.82-2.73 (m, 1H), 2.00-1.92 (m, 4H), 1.53-1.42 (m, 2H), 1.32-1.20 (m, 28H), 0.83 (t, J=6.9 Hz, 3H).13C NMR (75 MHz, DMSO-d6):δ 129.6, 72.3, 70.7, 65.5, 49.7, 47.1, 31.3, 29.13, 29.11, 28.90, 28.82, 28.67, 28.59, 26.58, 26.55, 25.6, 22.1, 18.6, 18.1, 13.9. CHN Analysis: Calculated: 68.61 C, 12.00 H, 3.33 N, 8.44 Cl. Found: 66.25 C, 11.95 H, 3.29 N, 8.43 Cl. LC-MS: Calculated for C24H50NO2 [M+H]+: 384; found: 384.

Below is a detailed description of AIP synthesis.

Oleyl-Glycidyl Ether:

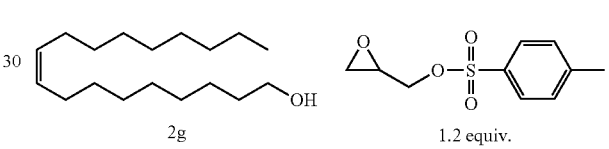

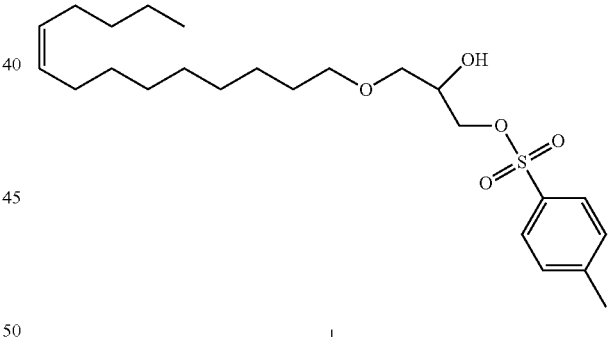

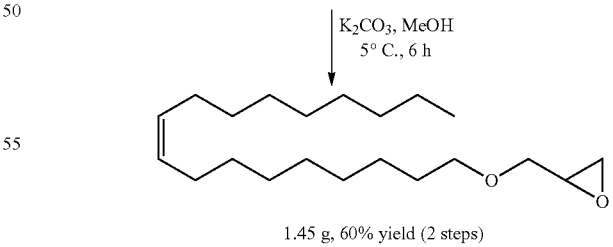

1.45 g, 60% yield (2 steps)

Oleyl alcohol (2.0 g, 7.44 mmol, Alfa Aesar) and glycidyl 4-toluenesulfonate (tosyl glycidol, 2.6 g, 11.4 mmol,) were dissolved in anhydrous dichloromethane (40 mL) under an argon atmosphere. To the solution, a catalytic amount of boron trifluoride diethyl etherate (100 mg, 0.70 mmol) was added. The solution stirred for 24 hours at room temperature. The solution was then concentrated under reduced pressure.

The remaining oil was dissolved in anhydrous methanol (40 mL). The flask was cooled in an ice/water bath and potassium carbonate (2.0 g, 14.4 mmol) was added. The mixture was stirred for 5 hours in an ice bath. The mixture was warmed slowly to room temperature over 1 hour when diethyl ether (50 mL) was added. The mixture was filtered through a pad of silica gel, washing with diethyl ether (2×100 mL). The combined filtrates were concentrated under reduced pressure. The remaining oil (3.11 g) was purified on silica gel (35 g), eluting with 10% ethyl acetate in hexane. The experiment generated 1.45 g (60% yield) of the glycidyl ether of oleyl alcohol as a colorless oil. $^1$H NMR δ (300 MHz, CDCl$_3$): 5.39 (t, 2H, J=5.4 Hz), 3.74 (dd, 1 H, J=11.7, 3.0 Hz), 3.60-3.48 (m, 2H), 3.42 (dd, 1H, J=11.4, 5.7 Hz), 3.19 (m, 1H), 2.84 (t, 1H, J=5.1 Hz), 2.65 (m, 1H), 2.04 (m, 4H), 1.62 (m, 2H), 1.45-1.28 (m, 22 H), 0.92 (t, 3H, J=6.0 Hz).

Octadecenyloxy-3-isopropylamine-propan-2-ol:

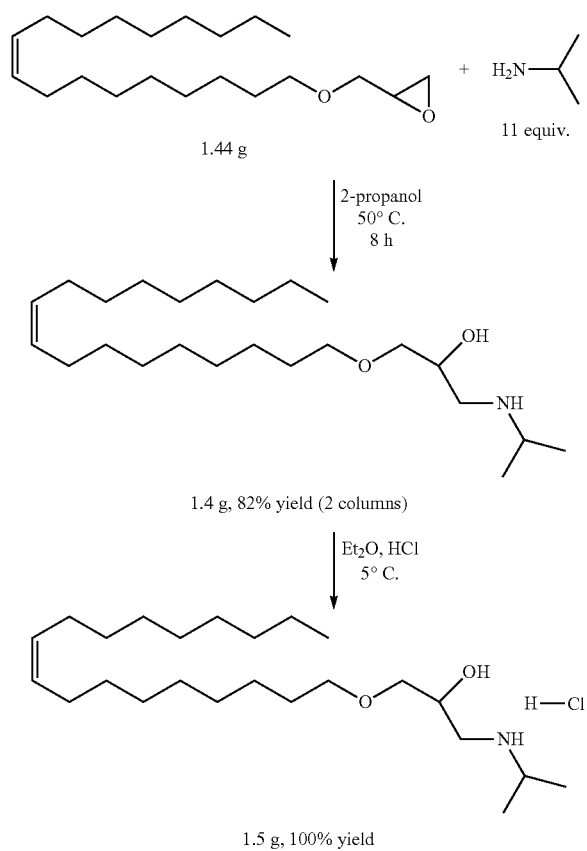

The glycidyl ether of oleyl alcohol (1.44 g, 4.43 mmol) was dissolved in 2-propanol (40 mL) under an argon atmosphere. Isopropylamine (3.0 g, 50 mmol) was added and the solution was stirred for 5 hours at 45-55° C. The heat was turned off and the flask cooled to room temperature and stirred overnight at room temperature. After 16 hours at room temperature, the solvent and excess isopropylamine were removed under reduced pressure. The remaining oil (1.9 g) was purified on silica gel (25 g), eluting with 1%-20% methanol in dichloromethane. This produced octadecenyloxy-3-isopropylamine-propan-2-ol (1.4 g, 82% yield) as a colorless oil. $^1$H NMR δ (300 MHz, CDCl$_3$): 5.34 (t, 2H, J=5.1 Hz), 3.84-3.76 (m, 1H), 3.48-3.35 (m, 4H), 2.84-2.71 (m, 2H), 2.59 (dd, 1H, J=12.0, 8.1 Hz), 2.10 (br s, 1H), 2.04-1.96 (m, 4H), 1.60-1.50 (m, 2H), 1.36-1.22 (m, 22H), 1.05 (d, J=6.3 Hz, 6H), 0.87 (t, 3H, J=6.3 Hz); $^{13}$C NMR δ (75 MHz, CDCl$_3$) 129.9, 129.8, 73.5, 71.7, 69.1, 49.6, 48.8, 31.9, 29.7, 29.6, 29.48, 29.44, 29.3, 29.2, 27.2, 26.1, 23.0 22.9, 22.7, 14.1.

Octadecenyloxy-3-isopropylamine-propan-2-ol hydrochloride:

Octadecenyloxy-3-isopropylamine-propan-2-ol (1.4 g, 3.6 mmol) was dissolved in diethyl ether (30 mL) under an argon atmosphere. The flask was cooled in an ice-water bath and a solution of hydrogen chloride in dioxane (2 mL of 4M) was added drop-wise. The mixture was stirred for 20-30 minutes. The solvent was then removed under reduced pressure and the remaining oil was dried under high vacuum for 20 hours at room temperature. This generated octadecenyloxy-3-isopropylamine-propan-2-ol hydrochloride as a colorless oil (1.5 g, 100% yield, >95% purity by NMR). $^1$H NMR (300 MHz, DMSO-d6): δ 8.92 (br s, 1H), 8.51 (br s, 1H), 5.56 (d, 1H, J=4.8 Hz), 5.30 (t, J=4.5 Hz, 2H), 4.02-3.80 (m, 1H), 3.40-3.26 (m, 5H), 3.00-2.90 (m, 1H), 2.82-2.73 (m, 1H), 2.00-1.92 (m, 4H), 1.53- 1.42 (m, 2H), 1.32-1.20 (m, 28H), 0.83 (t, J=6.9 Hz, 3H). 13C NMR (75 MHz, DMSO-d6): δ 129.6, 72.3, 70.7, 65.5, 49.7, 47.1, 31.3, 29.13, 29.11, 28.90, 28.82, 28.67, 28.59, 26.58, 26.55, 25.6, 22.1, 18.6, 18.1, 13.9. CHN Analysis: Calculated: 68.61 C, 12.00 H, 3.33 N, 8.44 Cl. Found: 66.25 C, 11.95 H, 3.29 N, 8.43 Cl.

B. Models.

Patient glioblastoma CA1 (BT73) and L1 cells were developed. The cells have been deposited in the UF Center for Brain Tumor Research. U87MG is an established and widely used and available human glioblastoma cell line. All cells have been genotyped for p53 and PTEN mutations as previously described. Proliferation and survival of adherent glioma and carcinoid sphere development from brain tumor-initiating cancer cells (BTIC) was evaluated and quantified. Glioma dissociated spheres expressing firefly luciferase reporter were implanted intracranially in mice and AIP suppression of tumor development and growth assessed. Normal rat cortical cultures, neuron-enriched cultures and human astrocytes were used for testing AIPs.

C. Data Analyses and Statistics.

AIPs effects on the cells and tissue metrics, including proliferation, survival and tumor markers can be analyzed using parametric and non-parametric ANOVA. In all statistical analyses, significant results in the ANOVAs are followed by Bonferroni's and Tukey post-hoc comparisons to determine which groups differed from each other. Tumor luminescent imaging metrics, time from implantation to death, and tumor size (if any) on autopsy can be quantitated. These data, longitudinal BCS scores, endpoint neurochemistry data are analyzed using paired statistical analysis (MANOVA). For mice survival, Kaplan-Meier curves and Wilcoxon-Gehan analyses were used.

D. Reagents, Kits, and Testing.

Reagents and Kits for flow cytometry, immunocytochemistry immunohistochemistry were purchased; antibodies used in the testing described, such as antibodies to PTEN, phosphoPTEN, Akt, GFAP, PDK1, FASN, GPR40, ZDAAC5, cleaved caspases 3 and 7 and LC3 were obtained from Abcam®, Cell Signaling Technology® or R&D Systems®, all with certificates of analyses. QSAR analyses of AIPs potencies dependent on the fatty chain length and saturation can be performed using commercial software packages (e.g., ACD Labs®), if desired.

Cell proliferation, viability and AIP toxicity are tested by known methods using bromodeoxyuridine (BrdU) and/or 3-(4,5-dimethylthiazol-2-yl)-5-(3-carboxymethoxyphenyl)-2-(4-sulfophenyl)-2Htetrazolium (MTS), and lactate dehydrogenase (LDH) release. Stem cell marker CD133, lineage-specific GFAP, CNPase, and nestin, and AIP targets palmitoyl transferase ZDHHC5, fatty acid synthase, fatty acid receptor GPR40, β-adrenoreceptors, PDK1, AKT/PTEN, cleaved caspases and autophagy LC3 are assessed by western blot, immunocytochemistry and flow cytometry. Preferably, the IC50 for AIP inhibition of patient glioblastoma BTIC is about 10 times lower than threshold toxicity in normal brain cells, and preferably at least 10 times lower than threshold toxicity in normal brain cells.

E. Animals 5-6 week-old NOD-scid IL2rγ null (NSG) animals were obtained and kept in a temperature-controlled facility with a 12 hour light/dark cycle and free access to food and water. Tumor cells were injected intracranially. Mice were anesthetized with 4% isofluorane. Cell suspensions (2-3 μl, 200,000 cells) were injected into the striatum (2 mm lateral from Bregma and 3 mm deep). Mice were monitored on a daily basis.

AIP-1 or AIP-2 (5 and 50 mg/kg) were given by intraperitoneal injection. In the mouse studies, AIP intraperitoneal injection at low dose (5 mg/kg) or high dose (50 mg/kg) began ten days post-tumor inoculation and continued once daily for 6 weeks or until the endpoints as described. At endpoints, mice were euthanized, tumors and blood collected, and organs briefly perfused with cold PBS and collected.

For glioma intracranial xenografts, NOD scid gamma, NOD-scid IL2Rgnull, mice were purchased from Jackson Laboratories. A live colony was maintained under SPF conditions; females that were homozygous for both the Prkdcscid and Il2rgtm1Wjl alleles were bred to males that were homozygous for Prkdcscid and hemizygous for Il2rgtm1Wjl (Il2rg is an X-linked gene). The following protocol will be used for genotyping endpoints as originally described by Jackson Laboratories: expected results: mutant=TAA wild type=TAT amplicon=149 bp.

```
                                              (SEQ ID NO: 1)
CTGTTCCAGTTATAGATCTTTGTTTTAGGGTCATTACTTGGTTTAA

TGTTTTTTAATGTAATTTGTATATGCTATTATAATAAGTAGAAAAA

AATGTGTTTTTTCCCTTAGAGTTTTGAGCAGACAATGCTGAGAAAA

GGAGGATCATGGATTCAAGAAATAAATGTAACGGAAAAGAATTGGT

ATCCACAACATAAAATACGCTA[t/a]GCTAAGAGAAAGTTAGCAG

GGGCCAACCCAGCTGTTATAACTTGGTAAGACTTGTGAATGCAGAA

TCAGTGTGTGTTCAAAAGTGCAAAGCACTTCACACACTTCTGAGCA

GTATGGCACTTCACTGTGTAGATGGAGAAAGTGACTCTTAGGGCGG

CTTTACCCCTCCAAGCCCAGCCTGCAAGGACTGGGCTCACACCCTT

GTC
```

F. Cells and Biologicals.

Human glioblastoma cell lines CA1 (also sometimes referred to as BT73) and L1 are cells are available from the Florida Center for Brain Tumor Research University of Florida Biorepository. Glioma cells (for example CA1, U87MG or L1), are suspended by trituration as single cells and plated at a density of about 25,000 cells/mL in low adhesion plates in Neurobasal® medium containing 1% methylcellulose and growth factors. The cultures are treated with single or repeated doses of AIPs (ranging from 0.1 to 20 ∞M) or vehicle (control) and maintained for 24 hours, 72 hours and 7 days. The number and size of 'carcinoid' spheres are quantitated by inverted phase contrast microscopy, and spheres collected for analysis for determination of survival and growth/proliferation.

In addition, glioma cells were cultured (adherent) in DMEM/F12 medium with 10% FBS to attain about 70% confluency. AIP (ranging from about 1 μM to about 100 μM) was added once or twice as above for 24 hours, 48 hours, or 72 hours and analyzed at these time points for proliferation, cell death and markers.

U-87MG, a hypodiploid human glioma cell line with the modal chromosome number 44 occurring in 48% of cells, is available from ATCC. These cells have been extensively characterized by the supplier and the rate of higher ploidy is 5.9%. Twelve markers were common to all cells, including der(1)t(1;3) (p22;q21), der(16)t(1;16) (p22;p12), del(9) (p13) and nine others. The marker der(1) had two copies in most cells. There was only one copy of normal X. N1, N6 and N9 were not found. The cells originally were free from mycoplasma and according to ATCC confirmed by STR profiling, Y-chromosome paint, and Q-band assay that the cell line is male in origin. Based on current literature, the cell line is likely a glioblastoma of CNS origin. The cells are free from Hep and HIV virus nucleic acids assessed by q-RT-PCR.

Primary cortical fractions (neurons+glia) and neuron-enriched cultures were prepared from newborn rat brains (P1) according to standard, known methods. Final cell preparations were resuspended in complete DMEM medium containing 10% horse serum, and plated at a density of $3-5 \times 10^5$ cells/mL to achieve 80-85% confluency.

Separate cell cultures were treated at day 3 of plating with 10 μM cytosine arabinoside for 2 days to obtain a neuron-enriched cell population, and then treated with AIPs.

Human astrocytes can be obtained from commercial sources. Normal human astrocytes #CC-2565 were obtained from Lonza (https://www.lonza.com/products-services/bio-research/primary-cells/human-cells-and-media/and validated by western blot with GFAP. Culture of human astrocytes is described in the art. See, for example Sharif A, and Prevot V. Isolation and culture of human astrocytes. Methods in Molecular Biology (Clifton, N.J.). 2012; 814:137-151. The cells in culture were challenged with a single or repeated dose of AIPs (ranging from about 1 to about 100 μM) and analyzed at about 24 to 72 hours post-treatment.

In all cell cultures, mycoplasma contamination has been controlled by two methods: continuous MycoFluor™ Mycoplasma Detection Kit (Thermo-Fisher™) and periodically (once a month) by q-RT-PCR The Universal Mycoplasma Detection Kit (ATCC).

PTEN and p53 genotyping of cells was performed by RT-PCR. The p53-specific primers covering the open reading frame were 5'-ACGGTGACACGCTTCCCTGGAT-TGG-3' (SEQ ID NO:2) and 5'-CTGTCAGTGGG-GAACAAGAAGTGGAGA-3' (SEQ ID ON:3). The PTEN-specific primer pairs covering the open reading frame were 5'-TTCTGCCATCTCTCTCCTCC-3' (SEQ ID NO:4) and 5'-TTTCATGGTGTTTTATCCCTC-3' (SEQ ID NO:5). See Kato et al., Functional evaluation of p53 and PTEN gene mutations in gliomas. Clin. Cancer Res. 6(10):3937-3943, 2000.

TABLE 1

Protocol Primers

| Primer Name | 5' Label | Sequence (5'-3') | 3' Label | Primer Type | Note | SEQ ID NO |
|---|---|---|---|---|---|---|
| 102 | | CAGACAATGCTGAGAAAAGGAG | | Forward | Reaction A | 6 |
| 103 | | CTGCATTCACAAGTCTTACCAAG | | Reverse | Reaction A | 7 |
| 104 | 6-FAM | TAAAATACGCTAAGCTAAGAGAAAG | Black Hole Quencher 1 | MUT probe | | 8 |
| 105 | JOE NHS Ester | TAAAATACGCTATGCTAAGAGAAAG | Black Hole Quencher 1 | WT probe | | 9 |

Example 2. Activation of Markers Expressed in Glioblastoma Cells

FABP7 is expressed predominantly in immature glia and in glioblastoma cells; CB1 and β-ADR are expressed predominantly in neuronal cells. Western blotting and immunohistochemistry analyses were used. The experiments performed here show that the AIP dose-dependently activates the CB1 receptor in CHO cells overexpressing CB1, followed by subsequent suppression of CP55,940 CB1 agonist stimulation (see FIG. 5A, which shows $Ca^{2+}$ mobilization followed by inhibition of calcium responses to CP55,940). AIPs also inhibit β-adrenergic calcium mobilization by isoprenaline in CHO cells overexpressing ADR (FIG. 5B) and therefore are active at β-adrenergic receptors.

Example 3. Effects of AIP Treatment on Proliferating Human Hepatocarcinoma (HUH-7) Cells Human hepatocarcinoma (HUH-7) cells were cultured at 50% or 90% confluency using standard procedure to produce proliferating cells. The cells were treated with AIP1 and AIP2 (10 mM for 24 hours). The treated cultures were examined for AKT kinase, basal PDK1 phosphorylation, expression of FASN, expression of GPR40, autophagy, caspase expression and apoptosis using standard methods.

Figure 6:
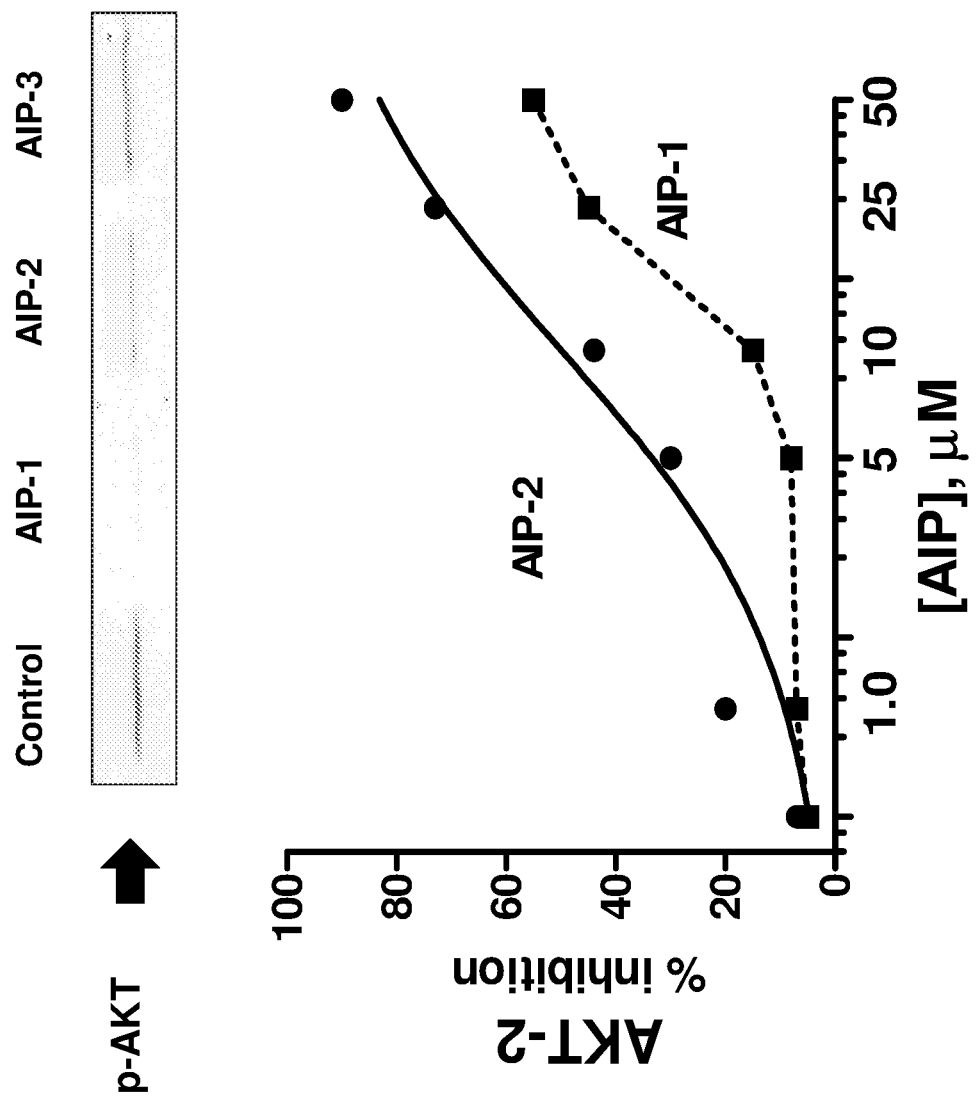
FIG. 6 is a graph showing that AIPs dose-dependently decreased AKT kinase activities and blocked basal AKT phosphorylation (AIP1 and AIP2) in proliferating HUH-7 (hepatocarcinoma) cells.

Results are provided in FIG. 6, FIG. 7 and FIG. 8. FIG. 6 shows that AIPs decreased AKT kinase activities and blocked basal AKT phosphorylation (AIP1 and AIP2) in proliferating HUH-7 cells in a dose-dependent manner. FIG. 7 shows that treatment with AIPs (10 mM for 24 hours) suppressed expression of FASN, up-regulated GPR40 and stimulated autophagy in human carcinoma HUH-7 cells. FIG. 8 shows that treatment with AIPs (10 mM for 24 hours) suppressed expression of caspases, and stimulated apoptosis and autophagy in human carcinoma HUH-7 cells.

Example 4. Dose-Dependent Suppression of Tumor-Initiating Cancer Stem Cells

In order to confirm dose-dependent AIP suppression of tumor-initiating cancer stem cells following a single and repeated administration of AIP and to compare these effects to toxicity in normal brain cells, tests were undertaken to demonstrate AIP efficacy to block glioblastoma multiforme stem cell activation and cause tumor cell death. This suppression of tumor-initiating glioblastoma multiforme stem/progenitor cells was determined using a 'carcinoid sphere' model in serum- and in anchorage-free media. The ability to block cancer stem cell activation and to destroy them is very useful for strategies to prevent glioblastoma recurrence. Here, AIPs blocked completely the activation of tumor-initiating CA1 cells and formation of carcinospheres at ≥2 µM concentrations. See FIG. 9A, which shows that AIPs block development of brain tumor-initiating stem cells with IC50s of 1.73 mM (AIP1) and 1.1 mM (AIP2). FIG. 9B is a set of representative photographs of the cells treated as indicated.

With respect to methods, generation of carcinoid spheres from GBM was performed essentially as described previously (Cao et al., Composite fatty acid ether amides suppress growth of liver cancer cells in vitro and in an in vivo allograft mouse model, Cell. Oncol. 36(3):247-257, 2013 and Reinartz et al., Functional Subclone Profiling for Prediction of Treatment-Induced Intratumor Population Shifts and Discovery of Rational Drug Combinations in Human Glioblastoma, Clinical Cancer Research: an official journal of the American Association for Cancer Research 23(2):562-574, 2017). Briefly, a suspension of freshly established patient glioblastoma cells CA1, was passaged once from cryopreservation, collected, triturated to a single cell suspension, and plated at a density of 25,000 cells/mL in low adhesion plates in complete Neurobasal® medium containing 1% methylcellulose and growth factors. The cultures were treated with single or repeated administrations of AIPs (0.1 µM to 20 µM) or vehicle control and maintained for 24 hours, 72 hours and 7 days. The number and size of spheres were quantitated by inverted phase contrast microscopy. Cell proliferation, viability and AIP toxicity were tested by BrdU incorporation, MTS tests and LDH release.

Example 5. Glioblastoma. CAI Cell Viability in Culture on AIP Treatment

Ales were screened in patient glioblastoma cells CA1 cells proliferating in adherent cultures. Briefly, cells were cultured in DMEM/F12 medium with 10% FBS to attain about 70% confluency. AIP1, AIP2, or vehicle (control) were added for 24 hours and analyzed for proliferation and survival. See FIG. 10, which shows that AIPs suppress proliferation and survival of adherent CA1 human glioblastoma multiforme (GBM). Cell viability/proliferation was measured by MTS added for additional 2-3 hours (FIG. 10A). Microphotographs of the cells were taken with Hoffman modulation-equipped phase-contrast microscope (FIG. 10B; x20 magnification is shown). These data show that both AIPI. and AIP2 strongly suppressed inhibition of CA I survival in growing adherent cells with a complete shutdown of metabolic activity at 20 µM and cell destruction. See FIG. 10.

Example 6. Safety of AIP Compounds for Normal Cortical Cells

Safety of AIPs has been ascertained using rat primary cortical cultures composed of glia and neurons. Final cell preparations of normal cortical cells were prepared as described in Example 1 above. After 72 hours in culture, the media in the final cell preparations were changed to fresh media with or without serum and the cells were treated with AIPs (1-100 µM) for additional 24 hours, 48 hours or 72 hours. AIP toxicity was compared to Temazolomide at 50 µM.

In the mixed cortical cultures, AIPs were not cytotoxic and did not affect normal cell viability and survival (testing by MTS) at concentrations of up to 20 µM (see FIG. 11A). The cell integrity and structural architecture were not altered following incubation with AIPs for a week (see FIG. 11B). Additional testing revealed that AIP1, 2 and 3 did not reduce survival of primary human hepatocytes up to 50 µM.

Example 7. Availability to the Brain of AIP Compounds

To assure brain bioavailability of the inventive compounds, time-dependent brain, liver and heart AIP accumulation was measured after intraperitoneal injection of 2.0 mg AIP2. Mice were sacrificed at specific times following injection. Tissues (blood, brain and liver) were taken, and the lipids extracted, loaded on silica-gel column, washed with diethyl ether, and eluted with 10% ethyl acetate in hexane. The eluates were further purified using gradient HPLC on a C8 reverse phase column and the AIP-corresponding fraction was collected and quantitatively analyzed by nano-1A/1B-light chain (LC, a microtubule-associated protein) detection, coupled with electrospray ionization-mass-spectroscopy using internal AIP standard. See FIG. 12A and 12B. The results show that the compound did accumulate in brain tissue and was able to cross the blood-brain barrier after systemic administration.

Example 8. Dose-Dependent Suppression of Tumor-Initiating Cancer Stem Cells

Example 4 above is repeated using L1 cells or the established U87MG cell line.

Example 9. Testing for Cell Markers

In a carcinoid sphere model as described in Example 4, spheres are collected for analysis of the non-differentiated tumor-initiating stem cells marker, CD133, and lineage-specific markers, GFAP, CNPase, and nestin. AIP targets, including fatty acid synthase (FASN), fatty acid receptors GPR40, and β3-adrenoreceptors (β-ADR). PDK1, AKT/PTEN and palmitoyl transferase DHHC5 are determined by immunohistochemistry and flow cytometry.

Example 10. Additional Cell Viability Testing in Culture on AIP Treatment

Example 5 is repeated using CA1 cells and L1 cells, and in the established U87MG line, (at concentrations ranging from 1 µM-100 µM) for 24 hours, 48 hours, and 72 hours. In separate cultures, repeated doses AIP are added at 48 hours and assessed at 72 hours post-treatment. Temazolomide at 50 µM is used as treatment standard. Cell proliferation is evaluated by BrdU incorporation, cytotoxicity by LDH release and tumor cell survival via mitochondrial respiration using the MTS test. Apoptosis markers (cleaved caspases 3 and 7, and autophagy level (LC3, beclin 1)) are assessed by immunocytochemistry and flow cytometry. IC50s are calculated from non-linear regression curves according to standard methods. FASN and GPR40, β1-ADR and β3-ADR, PDK1, AKT/PTEN and ZDHHC5 paimnoyl transferase are determined by western blot, flow cytometry and immunohistochemistry.

Example 11. AIP Suppression of Initiation and Growth of Human Glioblastoma Intracranial Xenografts The ability of AIP to suppress the initiation and growth of human glioblastoma cells is tested with glioblastoma multiforme patient-derived orthotopic intracranial xenografts in mice, which retain many of the molecular and phenotypic characteristics and histological signs of the parent tumor and are a suitable model for use in drug screening. The objective of this test is to validate AIPs' usefulness for blocking glioblastoma tumor formation in situ in mice as a proxy for chemotherapeutic treatment of glioblastoma multiforme and prevention of glioblastoma multiforme relapse.

Molecular genetic analysis of glioblastoma multiforme has identified critical genes and signaling, including PI-3-kinase/AKT and PTEN involved in the development and progression of glioblastoma multiforme. Here, orthotopic intracranial models of glioblastoma multiforme xenografts are produced by implanting dissociated patient gliomaspheres and testing the effect of AIP treatment compared to temozolomide (an oral chemotherapy drug used as a first line treatment for glioblastoma multiforme) for testing of the ability of AIPs to inhibit glioblastoma multiforme development and growth, and mitigation of tumor burden.

Specifically, dissociated gliomaspheres (5 µl, 200,000 cells) are implanted into the striatum 2 mm lateral from Bregma and 3 mm deep by stereotactic microsurgery of NOD-scid IL2rγ null (NSG) mice according to standard methods. AIP intraperitoneal injection at low dose (5 mg/kg) or high dose (50 mg/kg) are administered beginning one week post-inoculation and continuing once daily for 6 weeks or until an endpoint is reached (mice survival to six weeks after gliomasphere implantation, loss of >20% body weight, severe neurologic deficits, and/or body condition score (BSC)≤2. Time from the implantation of the tumor cells to the manifestation of severe neurological symptoms and death is recorded and used for analyses of AIP efficacy. These are compared to tumor mice treated with temozolomide (50 mg/kg) as a positive control.

Example 12. Quantitative Imaging of Tumor Grafting of U87MG Human Glioblastoma Cells in Mice A U87MG human glioblastoma cell line is stably transfected using lentiviral expression particles (LucNeo) to express firefly luciferase (AmsBio®) according to known methods described in the art. The labeled U87MG cells are injected into the striatum of NSG mice and tumor grafting is observed by whole body bioluminescent imaging according to established protocols. AIP treatment is begun one week after tumor cell implantation and continued for 6 weeks or until an endpoint is reached. Mice are observed every day for body weight, neurologic deficits, and body conditions. Once a week and at endpoints, mice are examined by quantitative imaging using a Perkin Elmer® (Caliper) IVIS Spectrum In Vivo System to confirm and measure tumor growth. This pre-clinical optical imaging system combines high throughput and full tomographic capability for fluorescent and bioluminescent luciferase reporter.

Mice survival is monitored continuously during treatment and Kaplan-Meyer curves are generated. At endpoints, brain tumors and surrounding tissue, liver and heart are collected, fixed and analyzed by immunohistochemistry for apoptosis markers (activated caspases), autophagy markers (beclin 1, LC3) and expression of AIP targets AKT, PTEN, and β-adrenoreceptors.

Example 13. Treatment of Glioblastoma Multiforme

A subject diagnosed with glioblastoma multiforme is administered orally 250 mg of AIP2 daily for 2 months.

REFERENCES

References listed below and throughout the specification are hereby incorporated by reference in their entirety.
1. Adkins J E, Boyer E W, McCurdy C R. Mitragyna speciosa, a psychoactive tree from Southeast Asia with opioid activity. Curr Top Med Chem. 2011; 11(9):1165-75.
2. Babu K M, McCurdy C R, Boyer E W. Opioid receptors and legal highs: Salvia divinorum and Kratom. Clin Toxicol (Phila). 2008 February; 46(2):146-52.
3. Baumann B C, Dorsey J F, Benci J L, Joh D Y, and Kao G D. Stereotactic intracranial implantation and in vivo bioluminescent imaging of tumor xenografts in a mouse model system of glioblastoma multiforme. J Vis Exp. 2012(67).
4. Binda E, Visioli A, Giani F, Lamorte G, Copetti M, Pitter K L, Huse J T, Cajola L, Zanetti N, DiMeco F, De Filippis L, Mangiola A, Maira G, Anile C, De Bonis P, Reynolds B A, Pasquale E B, Vescovi A L (2012). The EphA2 Receptor Drives Self-Renewal and Tumorigenicity in Stem-like Tumor-Propagating Cells from Human Glioblastomas. Cancer Cell. 22, 765-780.
5. Bjornson, C R, Rietze, R L, Reynolds, B A, Magli, M C and Vescovi, A L. (1999). Turning brain into blood: a hematopoietic fate adopted by adult neural stem cells in vivo. Science, 228:537-539.
6. Boyer E W, Babu K M, Adkins J E, McCurdy C R, Halpern J H. Self-treatment of opioid withdrawal using kratom (Mitragynia speciosa korth). Addiction. 2008 June; 103(6):1048-50.
7. Brewer G J, and LeRoux P D. Human primary brain tumor cell growth inhibition in serum-free medium optimized for neuron survival. Brain research. 2007; 1157:156-166.
8. Calvani M, Pelon F, Comito G, Taddei M L, Moretti S, Innocenti S, et al. Norepinephrine promotes tumor microenvironment reactivity through beta3-adrenoreceptors during melanoma progression. Oncotarget. 2015; 6(7):4615-4632.
9. Cao M, Prima V, Nelson D, and Svetlov S. Composite fatty acid ether amides suppress growth of liver cancer cells in vitro and in an in vivo allograft mouse model. Cellular oncology. 2013; 36(3):247-257.
10. Chen X, Ma H, Wang Z, Zhang S, Yang H, and Fang Z. EZH2 Palmitoylation Mediated by ZDHHC5 in p53-Mutant Glioma Drives Malignant Development and Progression. Cancer research. 2017; 77(18):4998-5010.
11. Chiang P C, Thompson D C, Ghosh S, and Heitmeier M R. A formulation-enabled preclinical efficacy assessment of a farnesoid X receptor agonist, GW4064, in hamsters and cynomolgus monkeys. J Pharm Sci. 2011; 100(11): 4722-4733.
12. Daina A, Michielin O, and Zoete V. SwissADME: a free web tool to evaluate pharmacokinetics, drug-likeness and medicinal chemistry friendliness of small molecules. Scientific reports. 2017; 7:42717.
13. Davis B, Shen Y, Poon C C, Luchman H A, Stechishin O D, Pontifex C S, et al. Comparative genomic and genetic analysis of glioblastoma-derived brain tumor-initiating cells and their parent tumors. Neuro Oncol. 2016; 18(3):350-360.
14. Davis M E. Glioblastoma: Overview of Disease and Treatment. Clinical journal of oncology nursing. 2016; 20(5):52-58.
15. Day B W, Stringer B W, Al-Ejeh F, Michael J, Ting M J, Wilson J, Kathleen S, Ensbey K S, Jamieson P R, Bruce Z C, Lim Y C, Offenhäuser C, Charmsaz S, Cooper L T, Ellacott J K, Harding A, Leveque L, Inglis P, Allan S, Walker D G, Lackmann M, Osborne G, Khanna K K, Reynolds B A, Lickliter J D Boyd A W. (2012). EphA3 Maintains Tumorigenicity and is a Therapeutic Target in Glioblastoma Multiforme. Cancer Cell. 23, 238-48.
16. Deleyrolle L P, Harding A, Cato K, Siebzehnrubl F A, Rahman M, Azari H, et al. Evidence for label-retaining tumour-initiating cells in human glioblastoma. Brain. 2011; 134(Pt 5):1331-1343.
17. Deleyrolle L P, Ericksson G, Morrison B J, Lopez A J, Burrage K, Burrage P, Vescovi A L, Rietze R L, Reynolds B A (2011). Determination of somatic and cancer stem cell symmetric division rate using sphere assays. PlosOne, January 5; 6(1):e15844
18. Festuccia C, Mancini A, Colapietro A, Gravina G L, Vitale F, Marampon F, et al. The first-in-class alkylating deacetylase inhibitor molecule tinostamustine shows antitumor effects and is synergistic with radiotherapy in preclinical models of glioblastoma. J Hematol Oncol. 2018; 11(1):32.
19. Fotovati A, Abu-Ali S, Wang P S, Deleyrolle L P, Lee C, Triscott J, et al. YB-1 bridges neural stem cells and brain tumor-initiating cells via its roles in differentiation and cell growth. Cancer research. 2011; 71(16):5569-5578.
20. Franceschi E, Minichillo S, and Brandes A A. Pharmacotherapy of Glioblastoma: Established Treatments and Emerging Concepts. CNS drugs. 2017; 31(8):675-684.
21. Friedmann-Morvinski D, and Singer O. Overexpression Models: Lentiviral Modeling of Brain Cancer. Curr Protoc Mouse Biol. 2013; 3(2):121-139.
22. Gravina G L, Mancini A, Colapietro A, Vitale F, Vetuschi A, Pompili S, et al. The novel CXCR4 antagonist, PRX177561, reduces tumor cell proliferation and accelerates cancer stem cell differentiation in glioblastoma preclinical models. Tumour Biol. 2017; 39(6): 1010428317695528.
23. Guo P, Nie Q, Lan J, Ge J, Qiu Y, and Mao Q. C-Myc negatively controls the tumor suppressor PTEN by upregulating miR-26a in glioblastoma multiforme cells. Biochemical and biophysical research communications. 2013; 441(1):186-190.
24. Haris S P, Zhang Y, Le Bourdonnec B, McCurdy C R, Portoghese P S. o-Naphthalenedicarboxaldehyde derivative of 7'-aminonaltrindole as a selective delta-opioid receptor affinity label. J Med Chem. 2007 Jul. 12; 50(14): 3392-6.
25. He J J, Zhang W H, Liu S L, Chen Y F, Liao C X, Shen Q Q, et al. Activation of beta-adrenergic receptor promotes cellular proliferation in human glioblastoma. Oncol Lett. 2017; 14(3):3846-3852.
26. Hitomi M, Deleyrolle L P, Mulkearns-Hubert E E, Jarrar A, Li M, Sinyuk M, et al. Differential connexin function enhances self-renewal in glioblastoma. Cell Rep. 2015; 11(7):1031-1042.

27. James M L, Shen B, Zavaleta C L, Nielsen C H, Mesangeau C, Vuppala P K, Chan C, Avery B A, Fishback J A, Matsumoto R R, Gambhir S S, McCurdy C R, Chin F T. New positron emission tomography (PET) radioligand for imaging σ-1 receptors in living subjects. J Med Chem. 2012 Oct. 11; 55(19):8272-82.

28. James M L, Shen B, Nielsen C H, Behera D, Buckmaster C L, Mesangeau C, Zavaleta C, Vuppala P K, Jamalapuram S, Avery B A, Lyons D M, McCurdy C R, Biswal S, Gambhir S S, Chin F T. Evaluation of σ-1 receptor radioligand 18F-FTC-146 in rats and squirrel monkeys using PET. J Nucl Med. 2014 January; 55(1):147-53.

29. Jarzabek M A, Huszthy P C, Skaftnesmo K O, McCormack E, Dicker P, Prehn J H, et al. In vivo bioluminescence imaging validation of a human biopsy-derived orthotopic mouse model of glioblastoma multiforme. Mol Imaging. 2013; 12(3):161-172.

30. Journigan V B, Mésangeau C, Vyas N, Eans S O, Cutler S J, McLaughlin J P, Mollereau C, McCurdy C R. Nonpeptide small molecule agonist and antagonist original leads for neuropeptide FF1 and FF2 receptors. J Med Chem. 2014 Nov. 13; 57(21):8903-27.

31. Kane B E, Nieto M J, McCurdy C R, Ferguson D M. A unique binding epitope for salvinorin A, a non-nitrogenous kappa opioid receptor agonist. FEBS J. 2006 May; 273(9):1966-74.

32. Kane B E, McCurdy C R, Ferguson D M. Toward a structure-based model of salvinorin A recognition of the kappa-opioid receptor. J Med Chem. 2008 Mar. 27; 51(6):1824-30.

33. Kato H, Kato S, Kumabe T, Sonoda Y, Yoshimoto T, Kato S, et al. Functional evaluation of p53 and PTEN gene mutations in gliomas. Clinical cancer research: an official journal of the American Association for Cancer Research. 2000; 6(10):3937-3943.

34. Kim W, Kang B R, Kim H Y, Cho S M, Lee Y-D, Kim S, et al. Real-time imaging of glioblastoma using bioluminescence in a U-87 MG xenograft model mouse. Journal of the Korean Society for Applied Biological Chemistry. 2015; 58(2):243-248.

35. Kucukturkmen B, and Bozkir A. Development and characterization of cationic solid lipid nanoparticles for co-delivery of pemetrexed and miR-21 antisense oligonucleotide to glioblastoma cells. Drug Dev Ind Pharm. 2018; 44(2):306-315.

36. Linkous A G, Yazlovitskaya E M, and Hallahan D E. Cytosolic phospholipase A2 and lysophospholipids in tumor angiogenesis. J Natl Cancer Inst. 2010; 102(18):1398-1412.

37. Louis, S A, Rietze, R L, Deleyrolle, L, Wagey, R E, Thomas, T E, Eaves, A C, and Reynolds, B A (2008). Discrimination and meaningful enumeration of neural stem versus progenitor cells using the neural colony forming cell (N-CFC) assay. Stem Cell, 26(4), 988-996.

38. Luchman H A, Stechishin O D, Nguyen S A, Lun X Q, Cairncross J G, and Weiss S. Dual mTORC½ blockade inhibits glioblastoma brain tumor initiating cells in vitro and in vivo and synergizes with temozolomide to increase orthotopic xenograft survival. Clinical cancer research: an official journal of the American Association for Cancer Research. 2014; 20(22):5756-5767.

39. Mankus J V, McCurdy C R. Nonpeptide ligands of neuropeptide FF: current status and structural insights. Future Med Chem. 2012 June; 4(9):1085-92.

40. Martuscello R T, Vedam-Mai V, McCarthy D J, Schmoll M E, Jundi M A, Louviere C D, Griffith B G, Skinner C L, Suslow O, Deleyrolle L P and Reynolds B A. A Supplemented High-Fat Low-Carbohydrate Diet for the Treatment of Glioblastoma. Clinical cancer research: an official journal of the American Association for Cancer Research. 2016; 22(10):2482-2495.

41. McCurdy C R, Jones R M, Portoghese P S. Investigation of phenolic bioisosterism in opiates: 3-sulfonamido analogues of naltrexone and oxymorphone. Org Lett. 2000 Mar. 23; 2(6):819-21.

42. McCurdy C R., U.S. Pat. No. 8,686,008.

43. McCurdy C R, Le Bourdonnec B, Metzger T G, El Kouhen R, Zhang Y, Law P Y, Portoghese P S. Naphthalene dicarboxaldehyde as an electrophilic fluorogenic moiety for affinity labeling: application to opioid receptor affinity labels with greatly improved fluorogenic properties. J Med Chem. 2002 Jul. 4; 45(14):2887-90.

44. McCurdy C R, Sufka K J, Smith G H, Warnick J E, Nieto M J. Antinociceptive profile of salvinorin A, a structurally unique kappa opioid receptor agonist. Pharmacol Biochem Behav. 2006 January; 83(1):109-13.

45. McDowell K A, Riggins G J, and Gallia G L. Targeting the AKT pathway in glioblastoma. Current pharmaceutical design. 2011; 17(23):2411-2420.

46. Mésangeau C, Narayanan S, Green A M, Shaikh J, Kaushal N, Viard E, Xu Y T, Fishback J A, Poupaert J H, Matsumoto R R, McCurdy C R. Conversion of a highly selective sigma-1 receptor-ligand to sigma-2 receptor preferring ligands with anticocaine activity. J Med Chem. 2008 Mar. 13; 51(5):1482-6.

47. Messali A, Villacorta R, and Hay J W. A Review of the Economic Burden of Glioblastoma and the Cost Effectiveness of Pharmacologic Treatments. PharmacoEconomics. 2014; 32(12):1201-1212.

48. Miller K D, Siegel R L, Lin C C, Mariotto A B, Kramer J L, Rowland J H, et al. Cancer treatment and survivorship statistics, 2016. CA: a cancer journal for clinicians. 2016; 66(4):271-289.

49. Montoya A, Amaya C N, Belmont A, Diab N, Trevino R, Villanueva G, et al. Use of non-selective beta-blockers is associated with decreased tumor proliferative indices in early stage breast cancer. Oncotarget. 2017; 8(4):6446-6460.

50. Okonogi N, Shirai K, Oike T, Murata K, Noda S E, Suzuki Y, et al. Topics in chemotherapy, molecular-targeted therapy, and immunotherapy for newly-diagnosed glioblastoma multiforme. Anticancer Res. 2015; 35(3):1229-1235.

51. Ozawa T, and James C D. Establishing Intracranial Brain Tumor Xenografts With Subsequent Analysis of Tumor Growth and Response to Therapy using Bioluminescence Imaging. Journal of Visualized Experiments: JoVE. 2010 (41):1986.

52. Pan W K, Li P, Guo Z T, Huang Q, and Gao Y. Propranolol induces regression of hemangioma cells via the down-regulation of the PI3K/Akt/eNOS/VEGF pathway. Pediatr Blood Cancer. 2015; 62(8):1414-1420.

53. Paul-Samojedny M, Suchanek R, Borkowska P, Pudelko A, Owczarek A, Kowalczyk M, et al. Knockdown of AKT3 (PKBgamma) and PI3KCA suppresses cell viability and proliferation and induces the apoptosis of glioblastoma multiforme T98G cells. Biomed Res Int. 2014; 2014:768181.

54. Piccirillo, S G M, Reynolds, B A, Zanetti, N, Lamorte, G, Binda, E, Broggi, G, Brem, H, Okivi, A, Dimeco, F, and Vescovi, A L. (2006). Bone morphogentic proteins inhibit the tumourigenic potential of human tumour-initiating cells. Nature, 444, 761-765.

55. Polivka J, Jr., Polivka J, Holubec L, Kubikova T, Priban V, Hes O, et al. Advances in Experimental Targeted Therapy and Immunotherapy for Patients with Glioblastoma Multiforme. Anticancer Res. 2017; 37(1):21-33.
56. Qu J, Rizak J D, Fan Y, Guo X, Li J, Huma T, et al. Establishment and partial characterization of a human tumor cell line, GBM-HSF, from a glioblastoma multiforme. Hum Cell. 2014; 27(3):129-136.
57. Ray S, Bonafede M M, and Mohile N A. Treatment Patterns, Survival, and Healthcare Costs of Patients with Malignant Gliomas in a Large US Commercially Insured Population. American Health & Drug Benefits. 2014; 7(3):140-149.
58. Reinartz R, Wang S, Kebir S, Silver D J, Wieland A, Zheng T, et al. Functional Subclone Profiling for Prediction of Treatment-Induced Intratumor Population Shifts and Discovery of Rational Drug Combinations in Human Glioblastoma. Clinical cancer research: an official journal of the American Association for Cancer Research. 2017; 23(2):562-574.
59. Reynolds, B A and Weiss, S. (1992). Generation of neurons and astrocytes from isolated cells of the adult mammalian central nervous system. Science. 255:1707-1710.
60. Reynolds, B A Tetzlaff, W, and Weiss, S. (1992). A multipotent EGF-responsive striatal embryonic progenitor cell produces neurons and astrocytes. Journal of Neuroscience, 12: 4565-4574.
61. Reynolds, B A and Weiss, S. (1996). Clonal and population analyses demonstrate that an EGF-responsive mammalian embryonic CNS precursor is a stem cell. Developmental Biology, 175: 1-13.
62. Reynolds, B A and Rietze, R L. (2005). Neural stem cells and neurospheres—Re-evaluating the relationship. Nature Methods, 2, 333-336.
63. Salphati L, Alicke B, Heffron T P, Shahidi-Latham S, Nishimura M, Cao T, et al. Brain Distribution and Efficacy of the Brain Penetrant PI3K Inhibitor GDC-0084 in Orthotopic Mouse Models of Human Glioblastoma. Drug metabolism and disposition: the biological fate of chemicals. 2016; 44(12):1881-1889.
64. Sautin et al., Am. J. Physiol., 2001; 281: C2010-C2019, http://ajpcell.physiology.org/content/281/6/C2010.1ong
65. Sautin et al., J. Hematology & Stem Cell Res. 2002, 11 (4) 643-650, http://onlineliebertpub.com/doi/abs/10.1089/15258160260194785
66. Seminerio M J, Robson M J, Abdelazeem A H, Mesangeau C, Jamalapuram S, Avery B A, McCurdy C R, Matsumoto R R. Synthesis and pharmacological characterization of a novel sigma receptor ligand with improved metabolic stability and antagonistic effects against methamphetamine. AAPS J. 2012 March; 14(1):43-51.
67. Sharif A, and Prevot V. Isolation and culture of human astrocytes. Methods in molecular biology (Clifton, N.,J.). 2012; 814:137-151.
68. Shields L B, Kadner R, Vitaz T W, and Spalding A C. Concurrent bevacizumab and temozolomide alter the patterns of failure in radiation treatment of glioblastoma multiforme. Radiat Oncol. 2013; 8:101.
69. Siebzehnrubl F A, Silver D J, Tugertimur B, Deleyrolle L P, Siebzehnrubl D, Sarkisian M R, et al. The ZEB1 pathway links glioblastoma initiation, invasion and chemoresistance. EMBO Mol Med. 2013; 5(8):1196-1212.
70. Singh N, Chevé G, Ferguson D M, McCurdy C R. A combined ligand-based and target-based drug design approach for G-protein coupled receptors: application to salvinorin A, a selective kappa opioid receptor agonist. J Comput Aided Mol Des. 2006 July-August; 20(7-8):471-93.
71. Svetlov et al. Am J Physiol. 1998; 274:G891-900 http://ajpgi.physiolog.org/content/274/5/G891
72. Svetlov et al. Hepatology 1999, 30(1): 128-136 http://www.ncbi.nlm.nih.gov/pubmed/10385648
73. Svetlov S I, Ignatova T N, Wang K K, Hayes R L, English D, and Kukekov V G. Lysophosphatidic acid induces clonal generation of mouse neurospheres via proliferation of Sca-1- and AC133-positive neural progenitors. Stem Cells Dev. 2004; 13(6):685-693.
74. Tabuchi S. The autotaxin-lysophosphatidic acid-lysophosphatidic acid receptor cascade: proposal of a novel potential therapeutic target for treating glioblastoma multiforme. Lipids in health and disease. 2015;14:56.
75. Tomuleasa C, Soritau O, Rus-Ciuca D, Ioani H, Susman S, Petrescu M, et al. Functional and molecular characterization of glioblastoma multiforme-derived cancer stem cells. J BUON. 2010; 15(3):583-591.
76. Van Brocklyn J R. Sphingolipid signaling pathways as potential therapeutic targets in gliomas. Mini Rev Med Chem. 2007; 7(10):984-990.
77. Vescovi, A L, Galli, R, Reynolds, B A (2006). Brain tumor stem cells. Nature Reviews Cancer. 6, 425-436.
78. Villa S, Balana C, and Comas S. Radiation and concomitant chemotherapy for patients with glioblastoma multiforme. Chin J Cancer. 2014; 33(1):25-31.
79. Vuppala P K, Jamalapuram S, Furr E B, McCurdy C R, Avery B A. Development and validation of a UPLC-MS/MS method for the determination of 7-hydroxymitragynine, a μ-opioid agonist, in rat plasma and its application to a pharmacokinetic study. Biomed Chromatogr. 2013 December; 27(12):1726-32.
80. Wang F, Liu H, Wang F, Xu R, Wang P, Tang F, et al. Propranolol suppresses the proliferation and induces the apoptosis of liver cancer cells. Mol Med Rep. 2018.
81. Wieland A, Trageser D, Gogolok S, Reinartz R, Hofer H, Keller M, et al. Anticancer effects of niclosamide in human glioblastoma. Clinical cancer research: an official journal of the American Association for Cancer Research. 2013; 19(15):4124-4136.
82. Wong S Y, Ulrich T A, Deleyrolle L P, MacKay J L, Lin J M, Martuscello R T, et al. Constitutive activation of myosin-dependent contractility sensitizes glioma tumor-initiating cells to mechanical inputs and reduces tissue invasion. Cancer research. 2015; 75(6):1113-1122.
83. Wu M, Fan Y, Lv S, Xiao B, Ye M, and Zhu X. Vincristine and temozolomide combined chemotherapy for the treatment of glioma: a comparison of solid lipid nanoparticles and nanostructured lipid carriers for dual drugs delivery. Drug Deliv. 2016; 23(8):2720-2725.
84. Yahyanejad S, van Hoof S J, Theys J, Barbeau L M, Granton P V, Paesmans K, et al. An image guided small animal radiation therapy platform (SmART) to monitor glioblastoma progression and therapy response. Radiother Oncol. 2015; 116(3):467-472.
85. Yahyanejad S, van Hoof S J, Theys J, Barbeau L M, Granton P V, Paesmans K, et al. An image guided small animal radiation therapy platform (SmART) to monitor glioblastoma progression and therapy response. Radiother Oncol. 2015; 116(3):467-472.
86. Yekkirala A S, Lunzer M M, McCurdy C R, Powers M D, Kalyuzhny A E, Roerig S C, Portoghese P S. N-naphthoyl-beta-naltrexamine (NNTA), a highly selective and potent activator of μ/kappa-opioid heteromers. Proc Natl Acad Sci USA. 2011 Mar. 22; 108(12):5098-103.

87. Young N, Pearl D K, and Van Brocklyn J R. Sphingosine-1-phosphate regulates glioblastoma cell invasiveness through the urokinase plasminogen activator system and CCN1/Cyr61. Mol Cancer Res. 2009; 7(1):23-32.

The invention claimed is:

1. A compound of Formula I:

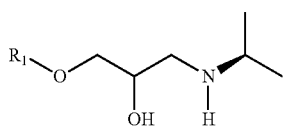

or a pharmaceutically acceptable salt thereof, wherein $R_1$ is an aliphatic chain having 18 carbon atoms that contains 3 unsaturations.

2. A pharmaceutical composition comprising a pharmaceutically acceptable carrier and the compound of claim 1.

3. A pharmaceutical composition comprising a pharmaceutically acceptable carrier and one or more compounds of claim 1.

4. A method of synthesizing the compound of claim 1, comprising the steps of:

(a) synthesizing a glycidyl ether fatty ether intermediate by mixing a fatty alcohol $R_1$—OH, wherein $R_1$ is an aliphatic chain having 18 carbon atoms that contains 3 double bonds, with glycidyl 4-toluenesulfonate (tosyl glycidol) in the presence of boron trifluoride diethyl etherate in anhydrous dichloromethane under an argon atmosphere to produce the intermediate

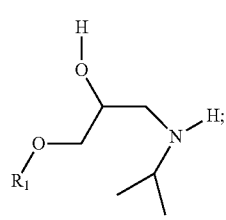

(b) purifying the intermediate;

(c) opening the glycidyl ring of the intermediate by stirring with isopropylamine in 2-propanol under an argon atmosphere to produce a 1-alkyl(alkenyl)oxy-3-isopropylamine-propan-2-ol base compound and (d) optionally condensing the base compound with HCl to produce a hydrochloride

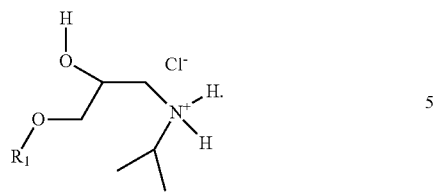

5. A method of treating brain cancer or brain cancer metastasis outside the central nervous system in a subject in need thereof, comprising administering a compound of claim 1.

6. The method of claim 5, which further comprises administering a second therapeutic agent.

7. The method of claim 5, wherein the subject is a mammal.

8. The method of claim 7, wherein the mammal is selected from the group consisting of a human, a laboratory animal, a companion animal, and a livestock animal.

9. The method of claim 8, wherein the mammal is human.

10. A method of preventing recurrence of brain cancer or brain cancer metastasis outside the central nervous system after chemotherapy, surgery, or radiation therapy for brain cancer in a subject in need thereof, comprising administering a compound of claim 1.

11. A method of suppressing growth of brain cancer cells comprising administering a compound of claim 1.

12. A method of enhancing survival of normal central nervous system cells comprising administering a compound of claim 1.

\* \* \* \* \*

```
                              SEQUENCE LISTING

<160> NUMBER OF SEQ ID NOS: 9

<210> SEQ ID NO 1
<211> LENGTH: 414
<212> TYPE: DNA
<213> ORGANISM: Mus musculus

<400> SEQUENCE: 1
ctgttccagt tatagatctt tgttttaggg tcattacttg gtttaatgtt ttttaatgta      60
atttgtatat gctattataa taagtagaaa aaaatgtgtt ttttccctta gagttttgag     120
cagacaatgc tgagaaaagg aggatcatgg attcaagaaa taaatgtaac ggaaaagaat     180
tggtatccac aacataaaat acgctatagc taagagaaag ttagcagggg ccaacccagc     240
tgttataact tggtaagact tgtgaatgca gaatcagtgt gtgttcaaaa gtgcaaagca     300
cttcacacac ttctgagcag tatggcactt cactgtgtag atggagaaag tgactcttag     360
ggcggcttta cccctccaag cccagcctgc aaggactggg ctcacaccct tgtc           414

<210> SEQ ID NO 2
<211> LENGTH: 25
<212> TYPE: DNA
<213> ORGANISM: Artificial Sequence
<220> FEATURE:
<223> OTHER INFORMATION: primer

<400> SEQUENCE: 2
acggtgacac gcttccctgg attgg                                            25

<210> SEQ ID NO 3
<211> LENGTH: 27
<212> TYPE: DNA
<213> ORGANISM: Artificial Sequence
<220> FEATURE:
<223> OTHER INFORMATION: primer

<400> SEQUENCE: 3
ctgtcagtgg ggaacaagaa gtggaga                                          27

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ttctgccatc tctctcctcc                                                  20

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
tttcatggtg ttttatccct c                                                21

<210> SEQ ID NO 6
<211> LENGTH: 22
<212> TYPE: DNA
```

```
<213> ORGANISM: Artificial Sequence
<220> FEATURE:
<223> OTHER INFORMATION: primer

<400> SEQUENCE: 6
cagacaatgc tgagaaaagg ag                                          22

<210> SEQ ID NO 7
<211> LENGTH: 23
<212> TYPE: DNA
<213> ORGANISM: Artificial Sequence
<220> FEATURE:
<223> OTHER INFORMATION: primer

<400> SEQUENCE: 7
ctgcattcac aagtcttacc aag                                         23

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8
taaaatacgc taagctaaga gaaag                                       25

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
taaaatacgc tatgctaaga gaaag                                       25
```